US006395367B1

(12) United States Patent
Michot et al.

(10) Patent No.: US 6,395,367 B1
(45) Date of Patent: May 28, 2002

(54) PENTACYCLIC ANION SALTS OR TETRAZAPENTALENE DERIVATIVES AND THEIR USES AS IONIC CONDUCTING MATERIALS

(75) Inventors: Christophe Michot, Grenoble (FR); Michel Armand, Montreal (CA); Michel Gauthier, La Prairie (CA); Yves Choquette, Sainte-Julie (CA)

(73) Assignees: Hydro-Quebec, Montreal (CA); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/125,799

(22) PCT Filed: Dec. 30, 1997

(86) PCT No.: PCT/CA97/01009

§ 371 (c)(1),
(2), (4) Date: Dec. 2, 1998

(87) PCT Pub. No.: WO98/29399

PCT Pub. Date: Jul. 9, 1998

(30) Foreign Application Priority Data

Dec. 30, 1996 (CA) ............................................. 2194127
Mar. 5, 1997 (CA) ............................................. 2199231

(51) Int. Cl.⁷ ........................ C07D 249/08; H01M 10/00
(52) U.S. Cl. ...................... 428/64.8; 429/188; 429/324; 430/541; 430/926; 359/265; 548/262.2; 548/267.8; 548/268.2
(58) Field of Search .................... 548/262.2, 267.8, 548/101, 103, 268.2; 570/124; 428/64.8; 430/541, 926; 429/188, 324; 359/265

(56) References Cited

U.S. PATENT DOCUMENTS

| 3,793,079 A | | 2/1974 | Brown et al. |
| 3,870,524 A | * | 3/1975 | Watanabe et al. ...... 204/159.23 |
| 4,851,307 A | | 7/1989 | Armand et al. |
| 5,072,040 A | | 12/1991 | Armand |
| 5,273,840 A | | 12/1993 | Dominey |
| 5,354,784 A | * | 10/1994 | Timmons et al. |
| 5,446,134 A | | 8/1995 | Armand et al. |
| 5,502,251 A | | 3/1996 | Pohmer et al. |
| 5,514,493 A | | 5/1996 | Waddell et al. |
| 5,538,812 A | * | 7/1996 | Lee et al. ................... 429/129 |
| 5,609,990 A | | 3/1997 | Ha et al. |
| 5,654,112 A | | 8/1997 | Itou et al. |
| 5,691,081 A | | 11/1997 | Krause et al. |
| 5,748,439 A | * | 5/1998 | MacFarlane et al. ........ 361/525 |
| 5,817,376 A | | 10/1998 | Everaerts et al. ........... 427/483 |
| 5,831,108 A | * | 11/1998 | Grubbs et al. ................ 522/33 |
| 5,874,606 A | | 2/1999 | Howells et al. |
| 5,962,546 A | | 10/1999 | Everaerts et al. |
| 6,063,522 A | | 5/2000 | Hamrock et al. |

FOREIGN PATENT DOCUMENTS

| EP | 0 571 832 | 5/1993 |
| WO | WO 96/24928 | 8/1996 |
| WO | WO 96/24929 | 8/1996 |
| WO | WO 97/23448 | 7/1997 |
| WO | WO 97/35929 | 10/1997 |
| WO | WO 97/35930 | 10/1997 |
| WO | WO 98/50349 | 11/1998 |
| WO | WO 99/49529 | 9/1999 |
| WO | WO 00/10969 | 3/2000 |
| WO | WO 00/11742 | 3/2000 |

OTHER PUBLICATIONS

Chambers et al., J. Chem. Soc., Chem. Commun., 1995, p841–842.*

* cited by examiner

Primary Examiner—Jeffrey Mullis
(74) Attorney, Agent, or Firm—Hutchins, Wheeler & Dittmar

(57) ABSTRACT

The invention relates to ionic compounds in which the anionic load has been delocalized. A compound disclosed by the invention includes an anionic portion combined with at least one cationic portion $M^{m+}$ in sufficient numbers to ensure overall electronic neutrality; the compound is further comprised of M as a hydroxonium, a nitrosonium $NO^+$, an ammonium $—NH_4^+$, a metallic cation with the valence m, an organic cation with the valence m, or an organometallic cation with the valence m. The anionic load is carried by a pentacyclical nucleus of tetrazapentalene derivative bearing electroattractive substituents. The compounds can be used notably for ionic conducting materials, electronic conducting materials, colorant, and the catalysis of various chemical reactions.

49 Claims, 1 Drawing Sheet

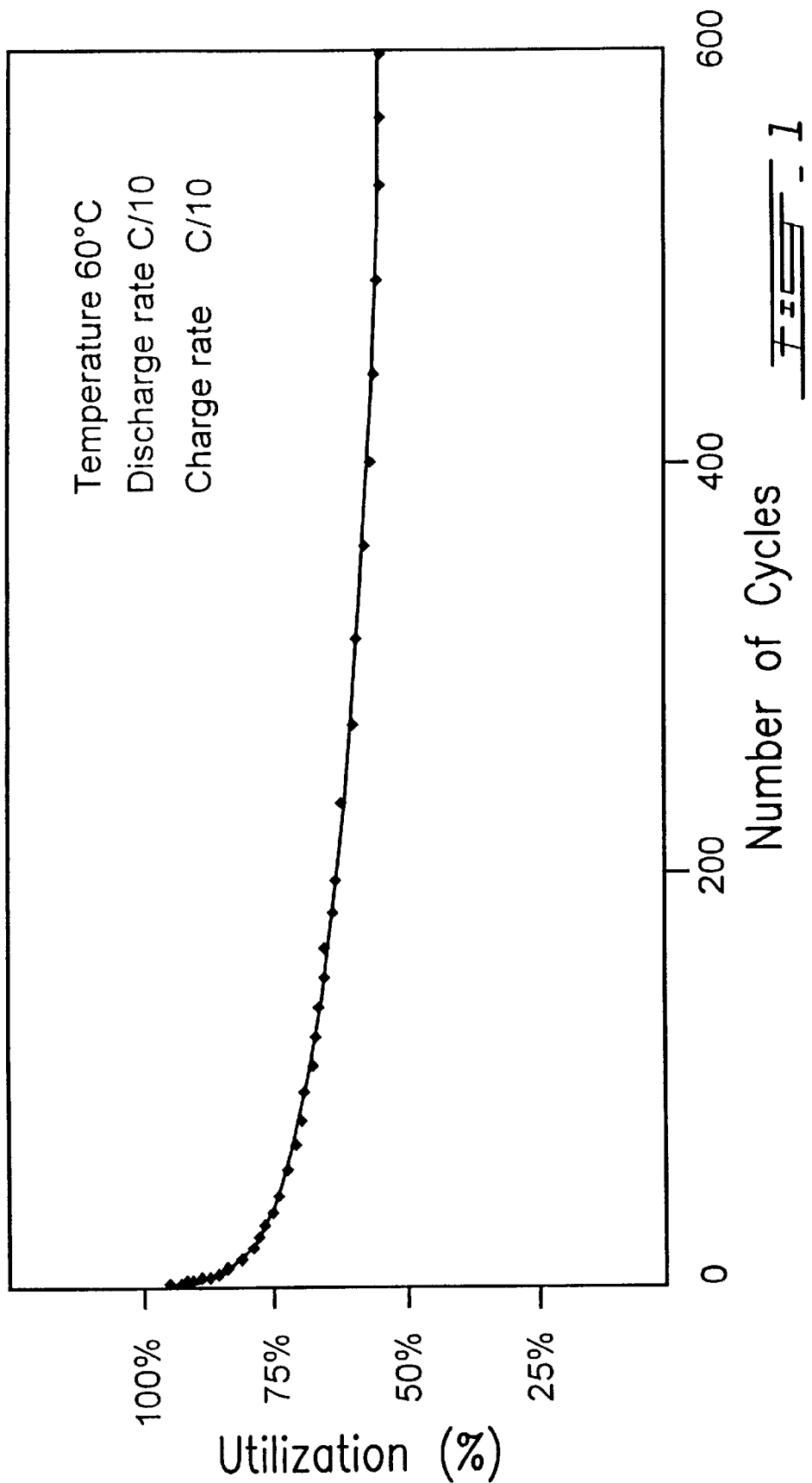

PENTACYCLIC ANION SALTS OR TETRAZAPENTALENE DERIVATIVES AND THEIR USES AS IONIC CONDUCTING MATERIALS

The present invention has for its object ionic compounds in which the ionic charge is carried by a pentacyclic nucleus or a derivative of tetrazapentalene, and their uses.

Derivatives of non-nucleophilic or slightly basic anions have an increasing importance in all applications of chemistry to stabilize or activate various cationic charges such as those of coloring materials or intermediate species in polymerizations. They also act as intermediates for various reactions of organic chemistry. In electrochemistry, media other than water are more and more relied upon for applications such as primary or secondary generators, supercapacitances, systems of modulation of light. The introduction of a weak ionic conductivity in the usual materials (polymers, combustible liquids), enables to disperse electrostatic charges.

The mainly known derivatives are those derived from coordination anions of the type $BF_4^-$, $PF_6^-$, $AsF_6^-$, however, they have a limited stability due to the dissociation equilibrium releasing the fluoride anion and the corresponding Lewis acid, the two causing parasite reactions and presenting some toxicity. The perchlorate anion $ClO_4^-$ is thermally unstable and dangerous.

On the other hand, anions derived from perfluoroalkylsulfonates and especially bis(perfluoroalkylsulfonyl)imides are known, which present interesting properties. However, the chemistry of these compounds is relatively difficult to control, in particular the preparation of precursors of the type $R_FSO_2-$. It is also known that hydrocarbons such as cyclopentadiene easily form salts by deprotonation, however, they acidity and the stability of the anion remain very insufficient (pKa≈16).

The inventors have found surprisingly that the properties of compounds derived from cyclopentadiene were considerably modified when a carbon of the cycle was replaced by a more electronegative element than carbon, or when an electronegative substituent was fixed to a carbon atom of the cycle. Depending on the choice of substituents, these compounds give salts which are easily soluble and strongly dissociated, including in organic media which are less polar than water. These salts have interesting properties for a number of applications and their preparation relies on materials which are more easily accessible. It is for example possible to obtain stable anionic heterocycles incorporating smaller quantities, which may even be null, of fluorine, or from fluorinated compounds which are easily accessible.

It is known and particularly interesting to introduce ionic groups in molecules or organic polymers having various functions. Coulombic forces correspond, indeed, to the stronger interactions which are available at the molecular level, and the ionic groups modify in the most noted way the molecules to which they are bonded. Coloring materials which are made soluble in water by means of sulfonate or carboxylate functions may be mentioned. However, the groups of this type $-CO_2^- 1/mM^{m+}$ or $-SO_3^- 1/mM^{m+}$ are not dissociated, and they do not induce solubility in solvents other than water or certain highly polar protic solvents such as light alcohols, which considerably restrict the scope of their utilization.

The possibilities of substitution associated with the chemistry of compounds derived from pentagonal cycles of the invention therefore also enable to introduce ionic groups in various molecules.

It is consequently an object of the present invention to provide a family of ionic compounds having a good solubility and good dissociation without having to rely on complex modifications of the starting molecule. The precursors of the molecules of the invention are generally easily accessible.

BRIEF DESCRIPTION OF THE FIGURE

FIG. 1 is a cycling curve showing utilization u verses the number of cycles c in a battery according to the invention.

An ionic compound of the present invention comprises at least one anionic part associated to at least one cationic part M in sufficient number to ensure the electronic neutrality of the whole, characterized in that M is a hydroxonium, a nitrosonium $NO^+$, an ammonium $-NH_4^+$, a metallic cation having a valency m, an organic cation having a valency m or an organometallic cation having a valency m, and in that the anionic part is pentacyclic or derived from tetrazapentalene and corresponds to one of the following formulae:

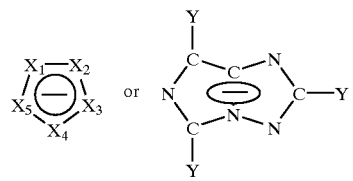

in which the groups $-X_i-$ represent independently from one another a group selected from $-N=$, $-N-$, $-C(Y_c)=$, $=C(Y_c)-$, $-S(=O)(Qs)=$, $-S(Qs)=$ or $-P(Q')(Q'')=$, it being understood that among the five groups $-X_i-$ forming the cycle, at most four groups $-X_i-$ comprise an hydrogen atom, at most two groups $-X_i-$ comprise a sulfur atom provided they are not adjacent on the cycle, at most one group $-X_i-$ comprise a phosphorus atom, and:

Q' and Q" represent independently from one another a $C_1-C_8$ perhaloalkyl or perhaloalkenyl radical, a $C_6-C_{12}$ aryl or alkylaryl radical, possibly halogenated, each may contain oxa, thia, aza substituents;

$Q_s$ is a radical selected from:
a) alkyl or alkenyl radicals, aryl, arylalkyl, alkylaryl or alkenylaryl radicals, alicyclic or heterocyclic radicals, including polycyclic radicals, said radicals being possibly halogenated or perhalogenated and/or possibly carrying at least one functional ether, thioether, amine, imine, amide, carboxyl, carbonyl, isocyanate, isothiocyanate, hydroxy functional group;
b) monocyclic, polycyclic or condensed aromatic radicals in which the aromatic nuclei and/or at least one substituent of a nucleus comprise heteroatoms such as nitrogen, oxygen, sulfur;
c) polymer radicals,
d) radicals having one or more cationic ionophoric groups and/or one or more anionic ionophoric groups;

$Y_c$ or Y represent H, or a group attracting electrons selected from the group consisting of:
F, Cl, Br, $-C\equiv N$, $-S-C\equiv N$, $-N=C=S$, $-N=C=O$, $-NO_2$, $C_nF_{2n+1}-$ $C_nF_{2n+1}-O-$, $C_nF_{2n+1}-CH_2-$, $-OC_2F_4H$, $-SCF_3$, $-SC_nF_{2n+1}$, $-SC_2F_4H$, $-O-CF=CF_2$, $-SCF=CF_2$, $FSO_2$;
radicals $QSO_2-$, $-CO_2Q$, $Q-N-SN_2-$, $QCO-$, in which Q is selected from the substituents defined about for $Q_s$;

radicals comprising one or more aromatic nuclei possibly containing at least one nitrogen, oxygen, sulfur or phosphorus atoms, said nuclei may possibly be condensed nuclei and/or the nuclei may possibly carry at least one substituent selected from halogens, —CN, —NO$_2$, —SCN, —N$_3$, CF$_2$=CF—O—, radicals RF— and R$_F$CH$_2$— in which R$_F$ is a perfluoroalkyl radical having 1 to 12 carbon atoms, fluoroalkyloxy groups, fluoroalkylthioxy groups, alkyl, alkenyl, oxa-alkyl, oxa-alkenyl, aza-alkyl, aza-alkenyl, thia-alkyl, thia-alkenyl radicals, polymer radicals, radicals having at least one cationic ionophoric group and/or at least one anionic ionophoric group;

or two substituents from Y$_c$, Q$_s$, Q' and Q" on the one hand and two substituents Y on the other hand, together forming a cycle having 4 to 8 chains, said cycle possibly being of aromatic conjugated nature;

or one from the substituents Y, Y$_c$ or Q$_s$ is a multivalent radical (including a dendrimer) connected to at least one pentacyclic anionic group or derived from tetrazapentalene as defined above;

or one of the substituents Y, Y$_c$ or Q$_s$ represent a recurring unit of a polymer.

In a compound of the present invention, the cation may be a metallic cation selected from cations of alkali metals, cations of alkali-earth metals, cations of transition metals, cations of trivalent metals, cations of rare earths. By way of example, Na$^+$, Li$^+$, K$^+$, Sm$^{3+}$, La$^{3+}$, Ho$^{3+}$, Sc$^{3+}$, Al$^{3+}$, Y$^{3+}$, Yb$^{3+}$, Lu$^{3+}$, Eu$^{3+}$ may be mentioned.

The cation may also be an organometallic cation, for example a metallocenium. By way of example, cations derived from ferrocene, titanocene, zirconocene, indenocenium or an arene metallocenium, cations of transition metals complexed with ligands of the phosphone type possibly having a chirality, organometallic cations having one or more alkyl or aryl groups covalently fixed to an atom or a group of atoms such as methylzinc, phenylmercury, trialkyltin or trialkyllead cations, may be mentioned. The organometallic cation may be part of a polymer chain.

According to a variant of the invention, the compounds of the invention have an organic cation selected from the group consisting of cations R$_3$O$^+$ (oxonium), NR$_4^+$ (ammonium), RC(NHR$_2$)$_2^+$ (amidinium), C(NHR$_2$)$_3^+$ (guanidinium), C$_5$R$_6$N$^+$ (pyridinium), C$_3$R$_5$N$_2^+$ (imidazolium), C$_3$R$_7$N$_2^+$ (imidazolinium), C$_2$R$_4$N$_3^+$ (triazolium), SR$_3^+$ (sulfonium), PR$_4^+$ (phosphonium), IR$_2^+$ (iodonium), (C$_6$R$_5$)$_3$C$^+$ (carbonium). In a given cation, the radicals R may all be identical. However, a cation may also include radicals R which may be different from one another. The radical R may be a H or it may be selected from the following radicals:

alkyl, alkenyl, oxa-alkyl, oxa-alkenyl, aza-alkyl, aza-alkenyl, thia-alkyl, thia-alkenyl, sila-alkyl, sila-alkenyl, aryl, arylalkyl, alkylaryl, alkenylaryl, dialkylamino and dialkylazo radicals;

cyclic or heterocyclic radicals possibly comprising at least one lateral chain comprising heteroatoms such as nitrogen, oxygen, sulfur;

cyclic or heterocyclic radicals possibly comprising heteroatoms in the aromatic nucleus;

groups comprising a plurality of aromatic or heterocyclic nuclei, condensed or non-condensed, possibly containing at least one nitrogen, oxygen, sulfur or phosphorus atom.

When an onium cation carries at least two radicals R which are different from H, these radicals may together form a cycle which may be aromatic or non-aromatic, eventually enclosing the center carrying the cationic charge.

When the cationic part of a compound of the invention is an onium cation, it may be in the form of an independent cationic group which is only bound to the anionic part by the ionic bond between the positive charge of the cation and the negative charge of the pentacyclic anionic part or it may be derived from a tetrazapentalene. In this case, the cationic part may be part of a recurring unit of a polymer.

An onium cation may also be part of a substituent Y, Y$_c$ or Q$_s$ carried by the pentacyclic anionic center or derived from tetrazapentalene. In this case, a compound of the invention constitutes a zwitterion.

When the cation of a compound of the invention is an onium cation, it may be selected so as to introduce in the compound, substituents capable of giving specific properties to said compound. For example, the cation M$^+$ may be a cationic heterocycle with aromatic character, including at least one nitrogen atom which is alkylated in the cycle. By way of example, an imidazolium, a triazolium, a pyridinium, a 4-dimethylamino-pyridinium may be mentioned, said cations possibly carrying a substituent on the carbon atoms of the cycle. Among these cations, those which give an ionic compound according to the invention in which the melting point is lower than 150° C. are particularly preferred. Such a compound having a low melting temperature is particularly useful for preparing materials with protonic conduction. A particularly preferred material with protonic conduction comprises a compound according to the invention in which the cation is formed by addition of a proton on the nitrogen of an imidazoline, an imidazole or a triazole, as well as the corresponding nitrogenated base in a proportion of 0.5 to 10 in molar ratio.

A compound of the invention in which the cation M is a cationic group having a bond —N=N—, —N=N$^+$, a sulfonium group, an iodonium group, or a substituted or non-substituted arene-ferrocenium cation, possibly incorporated in a polymeric network, is interesting insofar as it can be activated by a source of actinic energy of suitable wavelength. As particular examples of such compounds, there may be mentioned those in which the cation is a diaryliodonium cation, a dialkylaryliodonium cation, a triarylsulfonium cation, a trialkylaryl sulfonium cation, or a phenacyl-dialkyl sulfonium cation which is substituted or non-substituted. The above cations may be part of a polymer chain.

The cation M of a compound of the invention may include a group 2,2'[azobis(2-2'-imidazolinio-2-yl)propane]$^{2+}$ or 2,2'-azobis(2-amidiniopropane)$^{2+}$. The compound of the invention is then capable of releasing, under the action of heat or an ionizing radiation, radicals which enable to initiate reactions of polymerization, of cross-linking or, in a general manner, chemical reactions involving free radicals. Moreover, these compounds are easily soluble in polymeric or monomeric organic solvents even those of low polarity, contrary to the anion derivatives of the type Cl$^-$ usually associated with these type of compounds. They have a negligible vapour pressure contrary to the other free radical initiators of the peroxide or azo type, which is a considerable advantage for providing polymers in thin films, the volatility of the initiator having as a consequence a bad polymerization or cross-linking of the film surface.

According to an embodiment of the invention, at least one of the substituents Q$_s$ or Q is selected from alkyl, alkenyl, oxa-alkyl, oxa-alkenyl, aza-alkyl, aza-alkenyl, thia-alkyl or thia-alkenyl radicals having 1 to 24 carbon atoms, or from aryl, arylalkyl, alkylaryl or alkenylaryl radicals having 5 to 24 carbon atoms, or from alkyl or alkenyl radicals having 1 to 12 carbon atoms and possibly comprising at least one heteroatom O, N or S in the main chain or in a lateral chain, and/or possibly carrying an hydroxy group, a carbonyl group, an amine group, a carboxyl group. $Q_s$ or Q may also be part of a poly(oxyalkylene) radical or a polystyrene radical.

Another category of compounds according to the invention comprises compounds in which one of the substituents Y, $Y_c$ or $Q_s$ has at least one anionic ionophoric group and/or at least one cationic ionophoric group. The anionic group may for example be a carboxylic function ($-CO_2^-$), a sulfonate function ($-SO_3^-$), a sulfonimide function ($-SO_2NSO_2-$) or a sulfonamide function ($-SO_2N-$). The cationic ionophoric group may for example be an iodonium, sulfonium, oxonium, ammonium, amidinium, guanidinium, pyridinium, imidazolium, imidazolinium, triazolium, phosphonium or carbonium group. The cationic ionophoric group may totally or partially behave as cation M.

When at least one of these substituents Y, $Y_c$ or $Q_s$ includes at least one ethylenic unsaturation and/or one condensable group and/or one thermally, photochemically or ionically dissociable group, the compounds of the invention are reactive compounds which may be subject to polymerizations, cross-linkings or condensations, possibly with other monomers. They may also be used to fix ionophoric groups on polymers carrying a suitable reactive function.

In a compound of the invention, at least one of the substituents Y, $Y_c$ or $Q_s$ may be a mesomorphous group or a chromophore group or a self-doped electronically conductive polymer or a hydrolyzable alkoxysilane.

A substituent Y, $Y_c$ or $Q_s$ may include a group capable of trapping free radicals, for example a hindered phenol or a quinone.

A substituent Y, $Y_c$ or $Q_s$ may also include a dissociating dipole, for example an amide function, a sulfonamide function or a nitrile function.

A substituent Y, $Y_c$ or $Q_s$ may also include a redox couple, for example a disulfide group, a thioamide group, a ferrocene group, a phenothiazine group, a bis (dialkylaminoaryl) group, a nitroxide group or an aromatic imide group.

A substituent Y, $Y_c$ or $Q_s$ may also comprise an optically active group or a complexing ligand.

Another category of compounds comprises compounds in which Y or $Y_c$ represent an amino acid, or an optically or biologically active polypeptide.

According to a specific embodiment, the substituents Y or $Y_c$ of a compound of the invention are different from a perfluoroalkylsulfonyl group when M is a metallic cation.

In a compound of the invention, one of the substituents Y, $Y_c$ or $Q_s$ may be a radical having a valency v higher than two, comprising at each of its free ends an anionic pentacyclic group. Preferably, said multivalent radical comprises at least one $-SO_2-$ group, one $-CO-$ group, a perfluoroalkylene group having 1 to 8 carbon atoms, a phenylene group possibly substituted with heteroatoms, a group $-(W=W)_n-$ or a cationic group $-(W=W)_n-W^+-$, in which W is a nitrogen atom or a CR group in which R represents an organic radical and $0 \leq n \leq 5$, R being a hydrogen atom or an alkyl radical having 1 to 8 carbon atoms, or two substituents R together forming a cycle. In this case, the negative charges which are present on the pentacyclic anionic part or the part which is derived from tetrazapentalene of the compound of the invention should be compensated by the appropriate number of cations or ionophoric cationic groups M.

One of the substituents Y, $Y_c$ or $Q_s$ may also represent a recurring unit of a polymer chain. The compound of the invention may then be in the form of a polymer in which at least part of the recurring units carry a lateral group in which a pentacyclic anionic group or a group derived from tetrazapentalene is fixed.

According to an embodiment of the invention, Y or $Y_c$ is advantageously selected from the group consisting of $-CN$, $-OC_nF_{2n+1}$, $-OC_2F_4H$, $-SC_nF_{2n+1}$ and $-SC_2F_4H$, $-O-CF=CF_2$, $-SCF=CF_2$, n being a whole number from 1 to 8. Y or $Y_c$ may also be a radical $C_nF_{2n+1}CH_2-$, n being a whole number from 1 to 8, or from heterocycles in particular those derived from pyridine, pyrazine, pyrimidine, oxadiazole, thiadiazole, which are fluorinated or non-fluorinated.

The ionic compounds of the present invention comprise at least one ionophoric group in which substituents of various natures are fixed. In view of the very large possible choice of substituents, the compounds of the invention enable to provide properties of ionic conduction in most liquid or polymeric organic media having a polarity, which may even be very low. The applications are important in the field of electrochemistry, in particular for storing energy in primary or secondary generators, in supercapacitances, in combustible batteries and in electroluminescent diodes. The compatibility of the ionic compounds of the present invention with polymers or organic liquids enables to provide noted antistatic properties, even when the content in ionic compound is extremely low. The compounds of the invention which are polymers, as well as polymeric compounds obtained from compounds of the invention having the property of polymerizing or copolymerizing, have the above-mentioned properties with the advantage of possessing a fixed anionic charge. This is why another object of the present invention consists of an ionic conductive material made of an ionic compound of the present invention in solution in a solvent.

In an embodiment, the ionic compound used for preparing an ionically conductive material is selected from compounds in which the cation is ammonium, or a cation derived from a metal, in particular lithium or potassium, zinc, calcium, rare earth metals, or an organic cation, such as a substituted ammonium, an imidazolium, a triazolium, a pyridinium, a 4-dimethylamino-pyridinium, said cations possibly carrying a substituent on the carbon atoms of the cycle. The ionically conductive material thus obtained has a high conductivity and solubility in solvents, due to weak interactions between the positive charge and the negative charge. Its field of electrochemical stability is wide, and it is stable in reducing as well as oxidizing media. Moreover, the compounds which have an organic cation and a melting point lower than 150° C., in particular imidazolium, triazolium, pyridinium, 4-dimethylamino-pyridinium compounds have an intrinsic high conductivity, even in the absence of solvent, when they are in molten phase.

The properties of the ionically conductive material may also be adapted by the choice of substituents Y, $Y_c$ or Q on the one hand, and $Q_s$ on the other hand.

The choice for Q or $Q_s$ of an alkyl group, an aryl group, an alkylaryl group or an arylalkyl group enables to induce in the ionically conductive material, properties of the type mesogene, in particular alkyl groups of 6 to 20 carbon atoms, arylalkyl groups, in particular those containing a biphenyl unit, which produce phases of the type liquid crystal. Properties of conduction in phases of the type liquid crystal, nematic, cholesteric or discotic, are interesting for applications relative to optical postings or to reduce the mobility of anions in electrolytes, in particular in polymer electrolytes, without affecting the mobility of the cations. This particularity is important for applications in electrochemical generators, in particular those involving lithium cations.

When Q or $Q_s$ is a mesomorphous group or a group comprising at least one ethylenic unsaturation and/or a condensable group and/or a group which is thermally, photochemically or ionically dissociable, the ionically conductive material easily forms polymers or copolymers which are polyelectrolytes, either intrinsically when the polymer carries the solvating groups, or by addition of a polar solvent of the liquid or polymer type, or by mixture with such a solvent. These products have a conductivity which is solely due to the cations, which constitutes a very useful property for applications of the electrochemical generator type. When used in low molar fraction in a copolymer, they induce stable antistatic properties which are little dependent on humidity and promote the fixation of cationic coloring materials, this property being useful for textile fibers and lasers with coloring materials.

The presence of a substituent Q or $Q_s$ which is a self-doped electronically conductive polymer improves the stability of the ionically conductive material with respect to exterior agents. The conductivity is stable in time, even at elevated temperatures. In contact with metal, these materials give interface resistances which are very weak and in particular protect ferrous metals or aluminum against corrosion.

When a substituent Q or $Q_s$ is a hydrolyzable alkoxysilane, the ionically conductive material may form stable polymers by the simple mechanism of hydrolysis-condensation in the presence of water, thereby enabling to treat surfaces of oxides, silica, silicates, in particular glass, to produce properties of surface conduction, antistatic properties, or to promote the adhesion of polar polymers.

When a substituent Y, $Y_c$ or $Q_s$ is a group comprising a free radical trap such as a hindered phenol, or a quinone, the ionically conductive material has the following advantages and properties: it acts as antioxidant with no volatility and is compatible with polar monomers and polymers, to which it additionally gives antistatic properties.

When a substituent Y, $Y_c$ or $Q_s$ comprises a dissociating dipole such as an amide, a sulfonamide or a nitrile, the ionically conductive material has an improved conductivity in media of low and medium polarity, in particular in solvating polymers which enables to minimize, even to suppress, the addition of solvents or volatile plasticizing agents.

The presence of a substituent Y, $Y_c$ or $Q_s$ which contains a redox couple such as a disulfide, a thioamide, a ferrocene, a phenothiazine, a bis(dialkylaminoaryl) group, a nitroxide, an aromatic imide, enables to produce in the ionically conductive materials, properties of a redox shuttle which are useful as an element of protection and equalization of charge of electrochemical generators, in photoelectrochemical systems, in particular for the conversion of light into electricity in systems of modulation of light of the electrochrome type.

The presence of a substituent Y, $Y_c$ or $Q_s$ which is a complexing ligand in an ionically conductive material enables to chelate metallic cations, in particular those which possess an elevated charge (2, 3 and 4), in the form of soluble complex in organic media, including in aprotic media, and enables the transport of these cations in particular in the form of anionic complex, in solvating polymers. The metallic cations of elevated charge are indeed immovable in solvating polymers. This type of complexing gives with certain cations of transition metals (Fe, Co . . . ) or certain rare earths (Ce, Eu . . . ) particularly stable redox couples.

The ionically conductive materials containing a compound of the invention in which a substituent Q or $Q_s$ is an alkyl or alkenyl substituent which contains at least one heteroatom selected from O, N or S have a complexing and plasticizing capacity, in particular in polar polymers and especially polyethers. The heteroatoms N and S are selectively complexing for cations of transition metals, Zn and Pb.

When a substituent alkyl or alkenyl Q or $Q_s$ additionally carries an hydroxy group, a carbonyl group, an amine group, a carboxyl group, an isocyanate group or a thioisocyanate group, the ionic compound of the invention may give by polycondensation a polymer or a copolymer and the ionically conductive material which contains such a polymer or copolymer has polyelectrolytic properties.

The presence, in the ionically conductive material of the invention, of a compound in which a substituent Q or $Q_s$ is selected from aryl, arylalkyl, alkylaryl, alkylaryl or alkenylaryl radicals, in which the lateral chains and/or the aromatic nuclei comprise heteroatoms such as nitrogen, oxygen, sulfur, improves dissociation and increases the possibility of forming complexes depending on the position of the heteroatom (pyridine) or the possibility to give by duplicative oxidation, conjugated polymers or copolymers (pyrrole, thiophene).

When the ionically conductive material contains a compound of the invention in which a substituent Y, $Y_c$ or $Q_s$ represents a recurring unit of a polymer chain, the material constitutes a polyelectrolyte.

A compound of the invention in which the substituent Y, or $Y_c$ is selected from the group consisting of —$OC_nF_{2n+1}$, —$OC_2F_4H$, —$SC_nF_{2n+1}$ and —$SC_2F_4H$, —$OCF=CF_2$, —$SCF=CF_2$, n being a whole number from 1 to 8, is a precursor of stable monomers and polymers, in particular towards oxygen even at temperatures higher than 80° C. when dealing with polymers. An ionically conductive material which contains such a compound is therefore particularly suitable as the electrolyte of a combustible battery.

An ionically conductive material of the present invention comprises an ionic compound of the present invention in solution in a solvent.

The solvent may be an aprotic liquid solvent, a polar polymer or a mixture thereof.

The aprotic liquid solvent is selected for example from linear ethers and cyclic ethers, esters, nitrites, nitro derivatives, amides, sulfones, sulfolanes, alkylsulfamides and partially halogenated hydrocarbons. The solvents which are particularly preferred are diethyl ether, dimethoxyethane, glyme, tetrahydrofurane, dioxane, dimethyltetrahydrofurane, methyl or ethyl formate, propylene or ethylene is carbonate, alkyl carbonates (such as dimethyl carbonate, diethyl carbonate and methylpropyl carbonate), butyrolactones, acetonitrile, benzonitrile, nitromethane, nitrobenzene, dimethylformamide, diethylformamide, N-methylpyrrolidone, dimethylsulfone, tetramethylene sulfone and tetraalkylsulfonamides having 5 to 10 carbon atoms.

The polar polymer may be selected from cross-linked or non-cross-linked solvating polymers, which may carry grafted ionic groups. A solvating polymer is a polymer which includes solvating units containing at least one heteroatom selected from sulfur, oxygen, nitrogen and fluorine. By way of example of solvating polymers, there may be cited polyethers of linear structure, comb or blocks, which may form a network, based on poly(ethylene oxide), or copolymers containing the unit ethylene oxide or propylene oxide or allylglycidylether, polyphosphazenes, cross-linked networks based on polyethylene glycol cross-linked with isocyanates or networks obtained by polycondensation and carrying groups which enable the incorporation of cross-linkable groups. Block copolymers in which certain blocks carry functions which have redox properties may also be cited. Of course, the above list is non-limiting, and all the polymers having solvating properties may be used.

An ionically conductive material of the present invention may simultaneously comprise an aprotic liquid solvent selected from the aprotic liquid solvents mentioned above and a polar polymer solvent comprising units containing at least one heteroatom selected from sulfur, nitrogen, oxygen and fluorine. It may comprise from 2 to 98% liquid solvent. By way of example of such a polar polymer, polymers which mainly contain units derived from acrylonitrile, vinylidene fluoride, N-vinylpyrrolidone or methyl methacrylate may be mentioned. The proportion of aprotic liquid in the solvent may vary from 2% (corresponding to a plasticized solvent) to 98% (corresponding to a gelled solvent).

An ionically conductive material of the invention may additionally contain a salt which is well known to be used in the prior art for preparing ionically conductive material. Among the salts which may be used in admixture with an ionic compound of the invention, a salt selected from perfluoroalcanesulfonates, bis(perfluoroalkylsulfonyl) imides, bis(perfluoroalkylsulfonyl)methanes and tris (perfluoroalkylsulfonyl)methanes are particularly preferred.

Of course, an ionically conductive material of the invention may additionally contain additives known to be used in this type of material and for example mineral or organic charges in the form of powder or fibers.

An ionically conductive material of the invention may be used as electrolyte in an electrochemical generator. Thus, another object of the present invention is an electrochemical generator comprising a negative electrode and a positive electrode both separated by an electrolyte, characterized in that the electrolyte is an ionically conductive material as defined above. According to a particular embodiment, such a generator comprises a negative electrode consisting of metallic lithium, or an alloy thereof, possibly in the form of nanometric dispersion in lithium oxide, or a double nitride of lithium and of a transition metal, or an oxide of low potential having the general formula $Li_{1+y+x/3}Ti_{2-x/3}O_4$ ($0 \leq x \leq 1$, $0 \leq y \leq 1$), or carbon and carbonated products produced by pyrolysis of organic materials. According to another embodiment, the generator comprises a positive electrode selected from vanadium oxides $VO_x$ ($2 \leq x \leq 2,5$), $LiV_3O_8$, $Li_yNi_{1-x}Co_xO_2$, ($0 \leq x < 1$; $0 \leq y \leq 1$), spinels of manganese $Li_yMn_{1-x}M_xO_2$ (M=Cr, Al, V, Ni, $0 \leq x \leq 0,5$; $0 \leq y \leq 2$), organic polydisulfides FeS, $FeS_2$, iron sulfate $Fe_2(SO_4)_3$, phosphates and phosphosilicates of iron and lithium of olivine structure, or substituted products wherein iron is replaced by manganese, used alone or in admixtures. The collector of the positive electrode is preferably aluminum.

An ionically conductive material of the present invention may also be used in a supercapacitance. Another object of the present invention is consequently a supercapacitance utilizing at least one carbon electrode of high specific surface, or an electrode containing a redox polymer in which the electrolyte is an ionically conductive material such as defined above.

An ionically conductive material of the present invention may also be used for doping, p or n, an electronically conductive polymer and this use constitutes another object of the present invention.

In addition, an ionically conductive material of the present invention may be used as an electrolyte in an electrochrome device. An electrochrome device in which the electrolyte is an ionically conductive material according to the invention is another object of the present invention.

It has been observed that the strong dissociation of ionic species of the compounds of the invention results in a stabilization of carbocations, in particular those in which there is a conjugation with oxygen or nitrogen and, surprisingly a strong activity of the proton form of the compounds of the invention on certain monomers. The present invention also has as an object the use of ionic compounds as photo-initiators as sources of Brønsted acid which are catalysts for the polymerization or cross-linking of monomers or pre-polymers capable of cationic reaction, or as catalysts for the modification of polymers.

The process of polymerization or cross-linking of monomers or prepolymers capable of cationic reaction is characterized in that there is used a compound of the invention as photoinitiator constituting a source of acid catalyzing the polymerization reaction. The compounds according to the invention in which the cation is a group having a bond —N=N$^+$, —N=N—, a sulfonium group, an iodonium group, or an arene-ferrocenium cation which is substituted or non-substituted, possibly incorporated in a polymeric network, are particularly preferred.

The choice of substituents Y, $Y_c$ or $Q_s$ is made so as to increase the solubility of said compound in the solvents used for the reaction of monomers or prepolymers, and as a function of the desired properties for the final polymer. For example, the choice of non-substituted alkyl radicals gives a solubility in low polar media. The choice of radicals comprising an oxa group or a sulfone will provide solubility in polar media. The radicals including a sulfoxide group, a sulfone group, a phosphine oxide group, a phosphonate group, respectively obtained by the addition of oxygen on the atoms of sulfur or phosphorus, may give to the polymer obtained improved properties with respect to adhesion, shine, resistance to oxidation or to UV. The monomers and prepolymers which may be polymerized or cross-linked with the photoinitiators of the present invention are those which may undergo a cationic polymerization.

Among the monomers, monomers which include a cyclic ether function, a cyclic thioether function or cyclic amine function, vinyl compounds (more particularly vinyl ethers), oxazolines, lactones and lactames, may be mentioned.

Among the polymers of the ether or cyclic thioether type, ethylene oxide, propylene oxide, oxetane, epichlorhydrin, tetrahydrofurane, styrene oxide, cyclohexene oxide, vinyl-cyclohexene oxide, glycidol, butylene oxide, octylene oxide, glycidyl ethers and esters (for example glycidyl methacrylate or acrylate, phenyl glycidyl ether, diglycidylether of bisphenol A or its fluorinated derivatives), cyclic acetals having 4 to 15 carbon atoms (for example dioxolane, 1,3-dioxane, 1,3-dioxepane) and spiro-bicyclo dioxolanes, may be mentioned.

Among vinyl compounds, vinyl ethers constitute a very important family of monomers which are capable of cationic polymerization. By way of example, there may be mentioned ethyl vinyl ether, propyl vinyl ether, isobutyl vinyl ether, octadecyl vinyl ether, ethyleneglycol monovinyl ether, diethyleneglycol divinyl ether, butanediol monovinyl ether, butanediol divinyl ether, hexanediol divinyl ether, ethyleneglycol butyl vinyl ether, triethyleneglycol methyl vinyl ether, cyclohexanedimethanol monovinyl ether, cyclohexanedimethanol divinyl ether, 2-ethylhexyl vinyl ether, poly-THF-divinyl ether having a molecular weight between 150 and 5,000, diethyleneglycol monovinyl ether, trimethylolpropane trivinyl ether, aminopropyl vinyl ether, 2-diethylaminoethyl vinyl ether.

Other vinyl compounds may include, by way of example, 1,1-dialkylethylenes (for example isobutene), vinyl aromatic monomers (for example styrene, α-alkylstyrenes, such as α-methylstyrene, 4-vinylanisole, acenaphthene), N-vinyl compounds (for examples N-vinylpyrolidone or N-vinyl sulfonamides).

Among prepolymers, there may be mentioned compounds in which epoxy groups are carried by an aliphatic chain, an aromatic chain, or a heterocyclic chain, for example glycidic ethers of bisphenol A which are ethoxylated by 3 to 15 ethylene oxide units, siloxanes having lateral groups of the epoxycyclohexene-ethyl type obtained by hydrosilylation of copolymers of dialkyl, alkylaryl or diaryl siloxane with methyl hydrogenosiloxane in the presence of vinylcyclohexene oxide, condensation products of the sol-gel type obtained from triethoxy or trimethoxy silapropylcyclohexene oxide, urethanes incorporating the reaction products of butanediol monovinylether and an alcohol of a functionality higher than or equal to 2 with an aliphatic or aromatic di- or tri-isocyanate.

The process of polymerization according to the invention consists in mixing at least one monomer or prepolymer capable of cationic polymerization and at least one ionic compound of the invention, and subjecting the mixture obtained to actinic or β radiation. Preferably, the reaction mixture is subjected to radiation after having been formed into a thin layer having a thickness lower than 5 mm, preferably in the form of a thin layer having a thickness lower than or equal to 500 μm. The duration of the reaction depends on the thickness of the sample and the power of the source at the active λ wavelength. It is defined by the speed at which it passes in front of the source, which is between 300 m/min and 1 cm/min. Layers of the final material having a thickness higher than 5 mm may be obtained by repeating many times the operation consisting in spreading a layer and treating it with radiation.

Generally, the quantity of photoinitiator used is between 0.01 and 15% by weight with respect to the weight of the monomer or prepolymer, preferably between 0.1 and 5% by weight.

An ionic compound of the present invention may be used as photoinitiator in the absence of solvent, for example when it is intended to polymerize liquid monomers in which the ionic compound used as photoinitiator is soluble or easily dispersible. This type of utilization is particularly interesting, since it enables to overcome the problems associated with solvents (toxicity, flammability).

An ionic compound of the present invention may also be used as photoinitiator in the form of a homogeneous solution in a solvent which is inert towards polymerization, ready to be used and easily dispersible, in particular in the case where the medium to be polymerized or cross-linked has a high viscosity.

As example of an inert solvent, there may be mentioned volatile solvents, such as acetone, methyl-ethyl ketone and acetonitrile. These solvents will be used merely to dilute the products to be polymerized or cross-linked (to make them less viscous, especially when dealing with a prepolymer). They will be removed by drying after polymerization or cross-linking. Non-volatile solvents may also be mentioned. A non-volatile solvent also serves to dilute the products that one wishes to polymerize or cross-link, and to dissolve the ionic compound of the invention used as photoinitiator, however, it will remain in the material formed and will thus act as plasticizing agent. By way of example, propylene carbonate, δ-butyrolactone, ether-esters of mono-, di-, tri-ethylene or propylene glycols, ether-alcohols of mono-, di-, tri-ethylene or propylene glycols, plasticizing agents such as esters of phthalic acid or citric acid, may be mentioned.

According to another embodiment of the invention, there may be used as solvent or diluent a compound which is reactive towards polymerization, which is a compound of low molecular weight and of low viscosity which will simultaneously act as polymerization monomer and solvent or diluent for more viscous polymers or prepolymers used in combination. After the reaction, these monomers having been used as solvent will be part of the macromolecular network finally obtained, their integration being wider when dealing with bi-functional monomers. The material obtained after irradiation is now free of products having a low molecular weight and a substantial vapour tension, or capable of contaminating objects with which the polymer is in contact. By way of example, a reactive solvent may be selected from mono and divinyl ethers of mono-, di-, tri-, tetra-ethylene and propylene glycols, N-methylpyrolidone, 2-propenylether of propylene carbonate commercially available for example under the commercial designation PEPC from ISP, New Jersey, United States.

To irradiate the reaction mixture, the irradiation may be selected from ultraviolet radiation, visible radiation, X-rays, δ rays and β radiation. When ultraviolet light is used as actinic radiation, it may be advantageous to add to the photoinitiators of the invention photosensitizers intended to provide an efficient photolysis with wavelengths which are less energetic than those corresponding to the maximum of absorption of the photoinitiator, such as those produced by industrial devices, (I≈300 nm for mercury vapour lamps in particular). Such additives are known, and by way of non-limiting example, there may be mentioned anthracene, diphenyl-9,10-anthracene, perylene, phenothiazine, tetracene, xanthone, thioxanthone, acetophenone, benzophenone, 1,3,5-triaryl-2-pyrazolines and derivatives thereof, in particular derivatives which are substituted on the aromatic nuclei by alkyl, oxa- or aza-alkyl radicals, enabling inter alia to change the absorption wavelength. Isopropylthioxantone is an example of preferred photosensitizer when an iodonium salt according to the invention is used as photoinitiator.

Among the different types of radiation mentioned, ultraviolet radiation is particularly preferred. On the one hand, it is more convenient to use than the other radiations mentioned. On the other hand, photoinitiators are in general directly sensitive towards UV rays and photosensitizers are more efficient when the difference of energy (δλ) is lower.

The ionic compounds of the invention may also be used in association with free radical initiators produced thermally or by action of actinic radiation. It is also possible to polymerize or cross-link mixtures of monomers or polymers containing functions in which the types of polymerization are different, for example, monomers or prepolymers which polymerize by free radical and monomers or prepolymers which polymerize by cationic polymerization. This possibility is particularly advantageous for producing interpenetrated networks having physical properties which are different from those which would be obtained by a simple mixture of polymers originating from corresponding monomers. Vinyl ethers are not or are very little active by free radical initiation. It is therefore possible, in a reaction mixture containing a photoinitiator according to the invention, a free radical initiator, at least one monomer of the vinyl ether type and at least one monomer comprising non-activated double bonds such as those of the allyl groups, to carry out a separate polymerization for each type of monomer. On the other hand, it is known that monomers which are lacking in electrons, such as esters or amides of fumaric acid, maleic acid, acrylic or methacrylic acid, itaconic acid, acrylonitrile, methacrylonitrile, maleimide and derivatives thereof, form in the presence of vinyl ethers which are enriched in electrons, complexes of transfer of charge giving alternated polymers 1:1 by free radical initiation. An initial excess of vinyl monomers with respect to this stoichiometry enables to preserve polymerizable functions by pure cationic initiation. The start of the activity of a mixture of free radical initiator and cationic initiator according to the invention may be carried simultaneously for the two reactants in the case for example of insolation by actinic radiation of a wavelength for which the photoinitiators of the invention and the selected radical initiators are active, for example at I=250 nm. By way of example, the following commercial products: Irgacure 184®, Irgacure 651®, Irgacure 261®, Quantacure DMB®, Quantacure ITX® may be mentioned as initiators.

It may also be advantageous to use the two types of polymerization in a sequential manner, to first form prepolymers which are easy to shape and in which hardening, adhesion, solubility as well as degree of cross-linking may be modified by initiating the activity of the cationic initiator. For example, a mixture of a thermo-dissociable radical initiator and a cationic photoinitiator according to the invention enables to provide sequential polymerizations or cross-linking, first under the action of heat, then under the action of actinic radiation. Similarly, if a free radical initiator and a cationic photoinitiator according to the invention are selected, the first being photosensitive at longer wavelengths than the one initiating the photoinitiator according to he invention, there is obtained a cross-linking in two controllable steps. Free radical initiators may for example be Irgacure® 651 enabling to initiate free radical polymerizations at wavelength of 365 nm.

The invention also has as an object the use of ionic compounds of the invention for chemical amplification reactions of photoresists in the field of microlithography. During such use, a film of a material comprising a polymer and an ionic compound of the invention is subject to irradiation. The irradiation causes the formation of the acid by replacement of the cation M with a proton, which catalyzes the decomposition or transformation of the polymer. After decomposition or transformation of the polymer on the parts of the film which have been irradiated, the monomers formed or the polymer which has been converted are removed and what remains is an image of the unexposed parts. For this particular application, it is advantageous to use a compound of the invention which is in the form of a polymer consisting essentially of styrenyl recuriing units carrying a pentacyclic anionic group or a group derived from tetrazapentalene. These compounds enable to obtain after photolysis products which are not volatile, and therefore not odoriferous when dealing with sulfides. Among the polymers which may thus be modified in the presence of a compound of the invention, there may for example be cited polymers containing ester units or tertiaryalkyl arylether units, for example poly(phthaldehydes), polymers of bisphenol A and a diacid, polytertiobutoxycarbonyl oxystyrene, polytertiobutoxy-a-methyl styrene, polyditertiobutylfiumarate-co-allyltrimethyl-silane and polyacrylates of a tertiary alcohol, in particular tertiobutyl polyacrylate. Other polymers are described in J. V. Crivello et al, Chemistry of Materials 8, 376–381, (1996).

The ionic compounds of the present invention, which have an elevated thermal stability, give numerous advantages with respect to known salts of the prior art. They have speeds of initiation and propagation which are comparable or higher than those obtained with coordination anions of the type $PF_6^-$, $AsF_6^-$ and especially $SbF_6^-$.

In the compounds of the present invention, the pairs of ions have a very high dissociation, which enables the expression of intrinsic catalytic properties of the cation $M^{m+}$, in which the active orbits are easily exposed to substrates of the reaction, especially in different media. Most of the important reactions of organic chemistry may thus be carried out under relatively easy conditions, with excellent yields and the possibility of separating the catalyst from the reaction mixture. The demonstration of asymmetric induction by the use of an ionic compound according to the invention which carries a chiral group is particularly important in view of its generality and its ease of operation. The present invention consequently has as another object the use of compounds of the invention as catalysts in Friedel-Crafts reactions, Diels-Alder reactions, aldolization reactions, additions of Michael, reactions of allylation, reactions of pinacolic coupling, reaction of glycosilation, reaction of openings of the cycle of oxetanes, reactions of metathesis of alkenes, polymerizations of the Ziegler-Natta type, polymerizations of the metathesis type by cycle opening and polymerizations of the metathesis type of acyclic dienes. The preferred ionic compounds of the invention for utilization as catalyst for the above reactions are those in which the cation is selected from lithium, magnesium, copper, zinc, tin, trivalent metals, including rare earths, platinoids, and their organometallic couples, in particular metallocenes.

The compounds of the invention may also be used as solvent to carry out chemical, photochemical, electrochemical, photoelectrochemical reactions. For this particular use, the ionic compounds in which the cation is an imidazolium, triazolium, pyridinium or 4-dimethylamino-pyridinium, are preferred, said cation possibly carrying a substituent on the carbon atoms of the cycle. Among the compounds used in liquid form, those having a melting point lower than 150° C., more particularly lower than 100° C., are particularly preferred. The inventors have also found that the anionic charge carried by the pentacyclic group or the group derived from tetrazapentalene exerts a stabilizing effect on electronic conductors of the conjugated polymer type, and that use of a compound in which one of the substituents $Y$, $Y_c$ or $Q_s$ comprises a long alkyl chain enables to make these polymers soluble in the usual organic solvents even in doped state. Grafting of these charges on the polymer itself gives polymers in which the global charge is cationic, which are soluble in organic solvents and have, in addition to their stability, properties of anticorrosion towards metals, aluminum and ferrous metals. It is also an object of the present invention to provide electronically conductive material comprising an ionic compound of the present invention in which the cationic part is a polycation constituted of a doped "p" conjugated polymer. The preferred ionic compounds for this application are those in which one of the substituents $Q$ or $Q_s$ contains at least one alkyl chain having 6 to 20 carbon atoms. Additionally, the compounds in which $Y$ or $Y_c$ represents an aromatic nucleus carrying an alkyl radical may be mentioned.

The coloring materials of cationic type (cyanines) are used more and more frequently as sensitizers of photographic films, for storing optical information (optical disks accessible in writing), for lasers. The tendency of these conjugated molecules to pile over one another when they are in solid phase limits their utilization, because of the variation of the optical properties with respect to the isolated molecule. The use of ionic compounds of the invention for manufacturing cationic coloring materials including counter ions, possibly bound to this same molecule, correspond to functions of the invention, enables to reduce phenomenon of aggregation, including in solid polymer matrices and to stabilize these coloring materials. It is another object of the present invention to provide a composition of cationic coloring material, characterized in that it contains an ionic compound according to the invention. The particularly preferred ionic compounds for this application are those in which the negative charge(s) of the pentacyclic anionic group or a group derived from tetrazapentalene are either fixed to the molecule of the coloring material, or they constitute the counter-ion of the positive charges of the coloring material.

The compounds of the present invention may be obtained by processes of synthesis well known to those skilled in the art. Among these processes, some consist in building the cycle, others consist in modifying existing cycles.

By way of example, a pentacyclic compound in which two groups $X_i$ are groups —C(CN)= and a group $X_j$ is a group —S(=O)(CF$_3$)— may be obtained by reacting diaminomaleonitrile and sodium triflinate in the presence of a dehydrating agent, according to the first of the following reaction schemes.

A pentacyclic compound in which two groups $X_i$ are groups —C(CN)= and a group $X_j$ is a group —P(CF$_3$)$_2$— may be obtained by reacting 4,5-dicyano-1,3,2-diazaphospholate with a suitable trifluoromethylation agent, according to the second reaction scheme which follows.

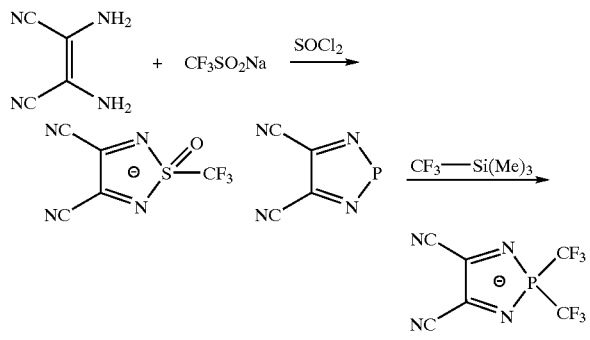

Other processes of preparation are described more in detail in the following examples, which illustrate compounds of the invention and their uses. The present invention is however not limited to these specific examples.

EXAMPLE 1

To 136.11 g (1 mole) of aminoguanidine bicarbonate H$_2$NNHC(=NH)NH$_2$.H$_2$CO$_3$ in 500 ml of toluene under stirring, there is added 119.73 g (1.05 moles) of trifluoroacetic acid CF$_3$CO$_2$H. After adding the acid and when escape of CO$_2$ has ceased, an azeotropic distillation was carried out by means of a Dean-Stark. After 24 hours, 54.5 ml (stoichiometry 55 ml) of water was recovered in the Dean-Stark container. After cooling the solution in toluene, while crystals appeared which have been recovered by filtration on a fritted glass of porosity N° 3. After drying, 139.9 g (92% yield) of 2-amino-5-trifluoromethyl-1,3,4-triazole, having a purity determined by a proton and fluorine RMN higher than 99%.

The corresponding potassium salts were prepared by reacting 2-amino-5-trifluoromethyl-1,3,4-triazole with potassium carbonate K$_2$CO$_3$ in water (20% in excess). After evaporating water and drying, the product obtained was reclaimed in acetonitrile, and the excess of carbonate was removed by filtration. After evaporation of acetonitrile and drying, the potassium salt of 2-amino-5-trifluoromethyl-1, 3,4-triazole was obtained in quantitative yield.

30.42 g (200 mmoles) of the potassium salt of 2-amino-5-trifluoromethyl-1,3,4-triazole (obtained according to the process described in Example 1) were dissolved in 20 ml of a 1 M solution of hydrochloric acid at 0° C. To the solution under stirring, 13.8 g (200 mmoles) of potassium nitrite NaNO$_2$ were added by portions. A precipitate of diazo-trifluoromethyltriazole is immediately formed. After 15 min, 9.8 g (200 mmoles) of sodium cyanide NaCN, 35.8 g (400 mmoles) of copper(I) cyanide CuCN and 2 ml of dioxane were added. An escape of nitrogen was then noted. After one night, 13.82 g (100 mmoles) of potassium carbonate were added to permit a precipitation of copper carbonate. After filtration, the solution was evaporated, the residue was dried, and it was reclaimed in 100 ml of methyl formate. After filtration, evaporation and drying, the residue was reclaimed in 200 ml of a 1 M solution of hydrochloric acid, and was extracted with two fractions of 50 ml of ether. After drying the organic phase with magnesium sulfate and evaporation of ether, the product obtained was sublimated under secondary vacuum at 40° C. After 48 hours, 9.89 g (61% yield) of 2-cyano-5-trifluoromethyl-1,3,4-triazole were recovered on a cold finger, with a purity determined by a proton and fluorine RMN higher than 99%.

The corresponding potassium salt was prepared by treating 2-cyano-5-trifluoromethyl-1,3,4-triazole by a process similar to the one described above for obtaining the potassium salt of 2-amino-5-trifluoromethyl-1,3,4-triazole.

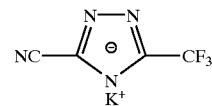

The salts of sodium and lithium were obtained by a similar process, by replacing potassium carbonate respectively with sodium carbonate and lithium carbonate.

These salts are soluble in most of the usual organic solvents (tetrahydrofurane, acetonitrile, dimethylformamide, ethyl acetate, glymes, . . . ) and in aprotic solvating polymers such as poly(ethylene oxide). In this latter solvent, at a concentration of O/Li of 14/1, the lithium salt has a ionic conductivity higher than $10^{-4}$ S.cm$^{-1}$ at a temperature of 60° C.

EXAMPLE 2

By a process similar to the one described in Example 1, but by replacing trifluoroacetic acid with 5-ene-2,2-difluoroheptanoic acid, the compound 2-(4-ene-1,1-difluorobutyl)-5-cyano-1,3,4-triazole was prepared, with a purity determined by a proton and fluorine RMN higher than 99%.

Potassium, sodium and lithium salts were obtained by treating triazole with corresponding carbonates.

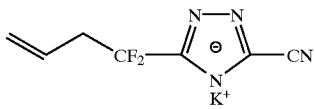

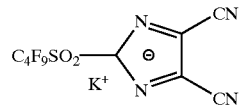

EXAMPLE 3

19.02 g (100 mmoles) of the potassium salt of 2-amino-5-trifluoromethyl-1,3,4-triazole prepared according to the process of Example 1 were dissolved in 25 ml of acetonitrile at −20° C. Then, 11.68 g (100 mmoles) of nitrosonium tetrafluoroborate $NOBF_4$ were added by portions. After 1 hour under stirring, the reaction mixture was filtered to remove the precipitate of potassium tetraborate $KBF_4$. Then, there was added 17.22 g (100 mmoles) of $CF_3SO_2K$ (commercially available from Parish) in solution in 25 ml of DMF and a trace of copper as catalyst. Formation of fine bubbles of nitrogen in the solution was noted. After 48 hours under stirring, the solution was evaporated and the residue was recrystallized in 50 ml of water to which 7.46 g (100 mmoles) of anhydrous potassium chloride KCl were added. After filtering and drying, 20.83 g (72% yield) of the potassium salt of 2-trifluoromethanesulfonyl-5-trifluoromethyl-1,3,4-hiazole were obtained, with a purity determined by a proton and fluorine RMN higher than 99%.

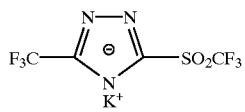

The lithium salt was obtained by ionic exchange in THF with lithium chloride. The acid was obtained by extraction with ether of an aqueous solution of the potassium salt acidified with hydrochloric acid.

The scandium salt was obtained by treating 10 mmoles of said acid, in solution in 10 ml of water, with 1.67 mmoles of scandium acetate. After stirring overnight, water was evaporated and the lanthanum salt of this compound was recovered in quantitative yield after drying.

EXAMPLE 4

11.81 g (100 mmoles) of 4,5-dicyanoimidazole and 10.12 g (100 mmoles) of triethylamine were placed in solution in 100 ml of tetrahydrofurane (THF). After bringing the solution to 0° C., there is slowly added, under argon, 14.06 g of benzoyl chloride. After 6 hours under stirring, the reaction mixture was filtered to remove the precipitate of triethylammonium chloride. Then, 30.21 g (100 mmoles) of perfluorobutanesulfonyl fluoride $C_4F_9SO_2F$ and 11.22 g (100 mmoles) of 1,4-diazabicyclo[2.2.2.]octane (DABCO) were added to the solution. After 72 hours under stirring, the reaction mixture was filtered to remove the precipitate of DABCO hydrochloride, and the solvent was evaporated. The residue was then reclaimed in 100 ml of a 2 M solution of potassium hydroxide and the solution was heated to reflux during 4 hours. After cooling the solution, a precipitate appeared which was recovered by filtration. There is thus obtained 31.56 g (72% yield) of the potassium salt of 2-perfluorobutanesulfonyl-4,5-dicyanoimidazole, with a purity determined by a proton and fluorine RMN higher than 99%.

The corresponding acid was obtained by ether extraction of an aqueous solution acidified with the potassium salt. The lithium salt was obtained by treating this acid with lithium carbonate $Li_2CO_3$.

EXAMPLE 5

In 50 ml of water, 11.81 g (100 mmoles) of 4,5-dicyanoimidazole were reacted with 5.3 g (50 mmoles) of anhydrous sodium carbonate $Na_2CO_3$. After 15 min under stirring, the solution was brought to 0° C. and 11 g (100 mmoles) of the sodium salt of dichloroisocyanuric acid was added. After one night, the solution was centrifuged in order to remove the sodium salt of isocyanuric acid which was formed during the reaction. After adding 14.91 g (200 mmoles) of anhydrous potassium chloride, the precipitate obtained was recrystallized. After filtration and drying, 11.88 g (62% yield) of the potassium salt of 2-chloro-4,5-dicyanoimidazole was recovered, with a purity determined by a proton and fluorine RMN higher than 98%.

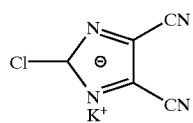

The lithium salt was obtained by ionic exchange in THF with lithium chloride.

EXAMPLE 6

To 8.89 g (40 mmoles) of the potassium salt of 2-(4-ene-1,1-difluoropropane)-5-cyano-1,3,4-triazole, obtained by a process as described in Example 2, in 100 ml of water, there is added 6.9 g (40 mmoles) of 3-chioroperoxybenzoic acid, obtained according to the process described by Scwartz & Blumbergs (J. Org. Chem., (1964), 1976). After one hour under strong stirring, the solvent was removed, and the residue was recrystallized in 10 ml of ethanol. After filtration and drying, the potassium salt of 2-(3,4-epoxy-1,1-difluorobutane)-5-cyano-1,3,4-triazole was recovered, with a purity characterized by a proton and fluorine RMN higher than 98%.

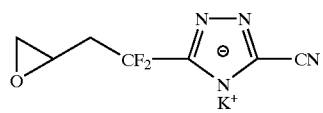

The lithium salt was obtained by treating the potassium salt in anhydrous tetrahydrofurane with a stoichiometric quantity of anhydrous lithium chloride, filtration of the reaction mixture, evaporation of the solvent and drying under vacuum.

The homopolymer of the potassium salt of 2-(3,4-epoxy-1,1-difluorobutane)-5-cyano-1,3,4-triazole was prepared by polymerization in tetrahydrofurane anionically initiated with potassium tert-butoxide, and the polysalt of lithium was obtained by ionic exchange in THF with anhydrous lithium chloride. The polysalt of lithium has a conductivity in gelled medium (21% by weight of polyacrylonitrile, 38% ethylene carbonate, 33% propylene carbonate, 8% homopolymer) of $1.2 \times 10^{-3}$ S.cm$^{-3}$ 1 at 30° C. The cationic transport number in this electrolyte is 0.92. Moreover, this polysalt is soluble in most of the usual organic solvents (tetrahydrofurane, acetonitrile, dimethylformamide, ethyl acetate, glymes, . . . ) and in aprotic solvating polymers.

EXAMPLE 7

In a glove box under argon, to a solution of 16.02 g (200 mmoles) of succinonitrile NCCH$_2$CH$_2$CN and 41.61 g (200 mmoles) of hexafluoroacetylketone CF$_3$COCH$_2$COCF$_3$ in 200 ml of anhydrous THF, there is added by portions 2.38 of lithium hydride (300 mmoles). After 48 hours, the reaction mixture was filtered, and the solvent was evaporated. The residue was recrystallized in 100 ml of water to which 14.91 g (200 mmoles) of anhydrous potassium chloride were added. After filtration and drying, 44.26 g (76% yield) of the potassium salt 2,5-trifluoromethyl-3,4-dicyano-cyclopentadiene were obtained, with a purity determined by a proton and fluorine PMN higher than 98%.

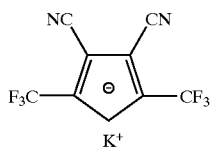

By a similar process, the potassium salt of the following compounds were prepared:

2-t-butyl-5-heptafluoropropyl-3,4-dicyano-cyclopentadiene (I) from 1,1,1,2,2,3,3-heptafluoro-7,7-dimethyl-4,6-octanedione;

2-trifluoromethyl-5-heptafluoropropyl-3,4-dicyano-cyclopentadiene (II) from 1,1,1,5,5,6,6,7,7,7-decafluoro-2,4-heptanedione;

2-(2-furyl)-5-trifluoromethyl-3,4-dicyano-cyclopentadiene (III), from 4,4,4-trifluoro-1-(2-furyl)-1,3-butanedione;

2-(2-thienyl)-5-trifluoromethyl-3,4-dicyano-cyclopentadiene (IV), from 1-(2-thenoyl)-3,3,3-trifluoroacetone.

These salts may easily be modified by reactions of nucelophilic substitution on the carbon carrying no substituent.

The acids were obtained by ether extraction of aqueous solutions of potassium salts which are acidified with hydrochloric acid.

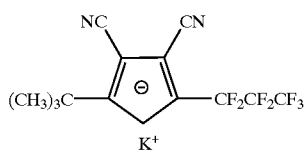
(I)

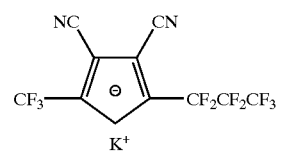
(II)

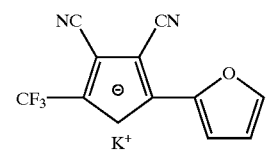
(III)

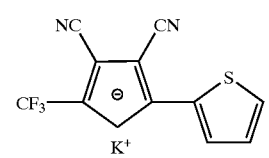
(IV)

EXAMPLE 8

3.03 g (10 mmoles) of stearic acid chloride C$_{17}$H$_{35}$COCl and 2.9 g of 2,5-trifluoromethyl-3,4-dicyano-cyclopentadiene (prepared according to the process of Example 7) were reacted in 20 ml of THF in the presence of 5 ml of pyridine. After 24 hours under stirring, the solution was filtered to remove the precipitate of potassium chloride, and contacted with 500 mg of lithium carbonate Li$_2$CO$_3$. The mixture was stirred during 24 hours, the excess of carbonate was removed by centrifugation, and the solvent was evaporated. 5.12 g of the lithium salt of 1-stearyl-2,5-trifluoromethyl-3,4-dicyano-cyclopentadiene were obtained, with a purity characterized by a proton and carbon RMN higher than 97%.

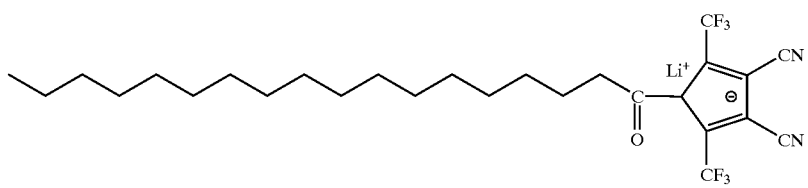

This salt has noted tensio-active properties, including in solvents and aprotic solvating polymers.

EXAMPLE 9

324 mg of 4-(dimethylamino)azobenzene-4'-sulfonyl chloride (1 mmole) were reacted with 290 mg of the potassium salt of 2,5-trifluoromethyl-3,4-dicyano-cyclopentadiene (1 mmole), in 10 ml of THF, in the presence of 5 µl of triethylamine. After 24 hours under stirring, the potassium chloride precipitate was removed and, after evaporation, the triethylammonium salt was obtained which was suspended in 5 ml of water containing in solution 350 mg of tetrabutylammonium bromide. The mixture was stirred during 24 hours. There is obtained a powder of orange color, with a purity characterized by a proton and carbon RMN higher than 98%. This powder is soluble in most of the organic solvents and corresponds to the following formula.

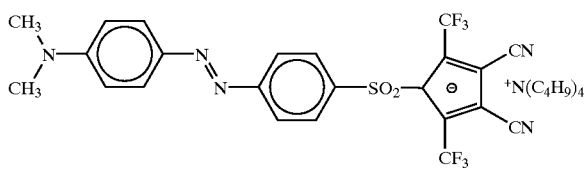

The compound may be used a pH indicator in non-aqueous medium (transition yellow-orange-red-violet in the pH zone 1–4).

EXAMPLE 10

501 mg (2 mmoles) of 6-hydroxy-2,5,7,8-tetramethylchroman-2-carboxylic acid (Trolox®) were suspended in 10 ml of ethyl acetate and 1 ml of pyridine. To this mixture, 580 mg (2 mmoles) of the potassium salt of 2,5-trifluoromethyl-3,4-dicyano-cyclopentadiene and 313 µl (2 mmoles) of 1,3-diisopropylcarbodiimide were added. After 24 hours, the diisopropylurea precipitate was filtered and the volume of the solution was reduced to 2 ml by means of a rotary evaporator. 20 ml of hexane were added and the mixture was cooled to −10° C. A white precipitate was collected by filtration. Its analysis corresponds to $C_{23}H_{17}N_2O_3KF_6$. It has antioxidizing properties, in particular for polymers.

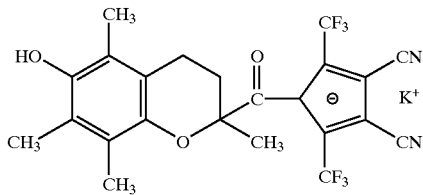

The same is true with respect to derivatives of other cations, including organic cations such as tetraalkylamomoniums.

EXAMPLE 11

2.8 (10 mmoles) of 4,4'-azobis(4-cyanovaleric) were suspended in 20 ml of methyl formate and 5 ml of pyridine. 5.16 g (20 moles) of lithium 2,5-trifluoromethyl-3,4-dicyano-cyclopentadiene and 4.16 g (20 mmoles) of dicyclohexyl-carbodiimide were added. The mixture was kept under magnetic stirring at 0° C. during 48 hours. The precipitate of dicyclohexylurea was removed by centrifugation and the solution was evaporated at room temperature. There is obtained a crystalline solid which is soluble in particular in acetone, acetonitrile, ethyl acetate, tetrahydrofurane. This compound may be used as a free radical initiator to initiate reactions of polymerization or of cross-linking even as low as 60° C.

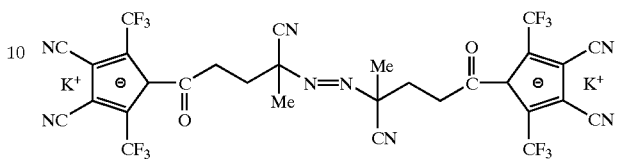

EXAMPLE 12

In a Parr chemical reactor, there is introduced 200 ml of anhydrous acetonitrile and 13 g (200 mmoles) of sodium nitride $NaN_3$. After closing the reactor, the latter was flushed with nitrogen, and 25 g (154 mmoles, commercially available from Aldrich) of hexafluorobutyne $CF_3C \equiv CF_3$ were introduced. After 24 hours under stirring, the reaction mixture was filtered and the solvent was evaporated. The residue was reclaimed in 154 ml (154 mmoles) of a 1 M solution of hydrochloric acid, and was extracted with two fractions of 50 ml ether. After drying the organic phase with magnesium sulfate and evaporating ether, there is obtained a product which was sublimated under vacuum at 40° C. 27.16 g (86% yield) of 4,5-trifluoromethyl-1H-1,2,3-triazole were recovered after 24 hours on a cold finger, with a purity determined by a proton and fluorine RMN higher than 99%.

The lithium salt was obtained by treating the acid with lithium carbonate in water.

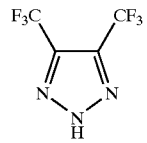

By a similar process, the following salts of lithium were prepared;

4-trifluoromethyl-5-cyano-1H-1,2,3-triazole (I) from 1-cyano-3,3,3 -trifluoropropyne $CF_3$ C≡CCN;

4-pentafluoroethyl-5-cyano-1H-1,2,3-triazole (II), from 1-cyano-4,4,4,3,3-pentafluorobutyne $C_2F_5C \equiv CCN$;

4-heptafluoropropyl-5-cyano-1H-1,2,3-triazole (III), from 1-cyano-5,5,5,4,4,3,3-heptafluoroheptyne $C_3F_7C \equiv CCN$.

The three alkynes used were obtained according to the procedure described by Huang, Shen, Ding, Zheng (*Tetrahedron Lett.*, (1981), 22, 5283).

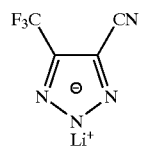
(I)

(II)

-continued

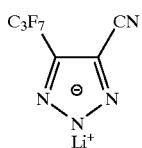
(III)

These salts are soluble in most of the usual organic solvents (tetrahydrofurane, acetonitrile, dimethylformamide, ethyl acetate, glymes, . . . ) and in aprotic solvating polymers such as poly(ethylene oxide). The concentrated solutions of these salts in acetone may be used as catalyst in Diels-Alder reactions.

EXAMPLE 13

13 g (200 mmoles) of sodium nitride $NaN_3$ and 23.29 g (100 mmoles) of 2,3-dichloro-hexafluoro-2-butene $CF_3CCl=CClCF_3$ in 50 ml of DMF were reacted in the presence of 13.09 g (200 mmoles) of zinc. After 72 hours under stirring, the reaction mixture was filtered and the solvent was evaporated. The residue was reclaimed in 154 ml (154 mmoles) of a 1 M solution of hydrochloric acid, and it was extracted with two fractions of 50 ml ether. After drying the organic phase with magnesium sulfate and evaporation of ether, there is obtained a product which was sublimated under vacuum at 40° C. After 24 hours, 14.76 g (72% yield) of 4,5-trifluoromethyl-1H-1,2,3-triazole were recovered on a cold finger, with a purity determined by a proton and fluorine RMN higher than 99%.

In 20 ml of ether, 4.1 g of this compound (20 mmoles) and 1.38 g of 1,2,3-triazole (20 mmoles) were dissolved. There is immediately formed a precipitate which was recovered by filtration and dried. The following salt was obtained:

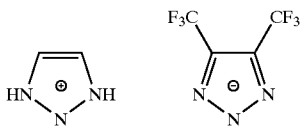

A molar mixture of three 1,2,3-triazole for one triazolium salt was crushed in a mortar placed in a glove box. There is obtained a liquid in the mortar. This molten salt has a high protonic conductivity higher than $10^{-3}$ $S.cm^{-1}$ at 30° C. It may be used to prepare a polymer electrolyte, which is an anhydrous proton conductor, by adding poly(ethylene oxide), preferably of high molecular weight or which could later on be cross-linked, to the molten salt without harming its conductivity. These polymer electrolytes are particularly interesting for providing systems of modulation of light such as electrochrome glazings including electrochrome systems with coloring materials.

A polymer electrolyte consisting of 80% by weight of said molten salt and 20% by weight of poly(ethylene oxide) of molecular weight $5\times10^6$ was used to prepare a membrane which is optically transparent in the visible range and has a good mechanical behaviour. Then, an electrochrome system was prepared in a glove box by utilizing this membrane enclosed between a first electrode consisting of the deposit of a layer of hydrogenated iridium oxide $H_xIrO_2$ on a glass plate and a conductive sub-layer of tin oxide, and a second electrode consisting of a layer of tungsten trioxide $WO_3$ and a conductive sub-layer of tin oxide. This electrochrome enabled a variation of optical absorption between 80% (discolored state) and 30% (colored state) and good performances in cycling (more than 20,000 cycles).

EXAMPLE 14

11.81 g (100 mmoles) of 4,5-dicyanoimidazole and 10.12 g (100 mmoles) of triethylamine were placed in solution in 100 ml of THF. After bringing this solution to 0° C., there is slowly added, under argon, 14.06 g of benzoyl chloride. After 6 hours under stirring, the reaction mixture was filtered to remove the triethylammonium chloride precipitate. Then, there is added to the solution 16.85 g (100 mmoles) of trifluoromethanesulfonyl chloride and 11.22 g (100 mmoles) of DABCO. After 72 hours under stirring, the reaction mixture was filtered to remove the precipitate of DABCO hydrochloride, and the solvent was evaporated. The residue was then reclaimed in 10 ml of a 2 M solution of potassium hydroxide and the solution was heated to reflux during 4 hours. After cooling the solution, a precipitate appeared which was recovered by filtration. There is thus obtained 21 g of potassium 2-trifluoromethanesulfonyl-4,5-dicyanoimidazole, with a purity determined by a proton and fluorine RMN higher than 99%.

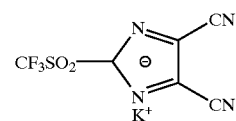

By a similar process, but by replacing trifluoromethanesulfonyl chloride with 2,2,2-trifluoroethyl trifluoroacetate $CF_3CO_2CH_2CF_3$, there is obtained potassium 2-trifluoroacetyl-4,5-dicyanoimidazole (yield 69%), with a purity determined by a proton and fluorine RMN higher than 99%.

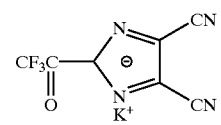

By a similar process, but by replacing trifluoromethanesulfonyl chloride with trifluoroethanesulfonyl chloride $CF_3CH_2SO_2Cl$, there is obtained potassium 2-trifluoroethanesulfonyl-4,5-dicyanoimidazole (yield 73%), with a purity determined by a proton and fluorine RMN higher than 99%.

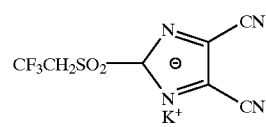

By a similar process, but by replacing trifluoromethanesulfonyl chloride with sulfamoyl chloride $(CH_3)2NSO_2Cl$, there is obtained potassium 2-dimethylaminosulfonyl-4,5-dicyanoimidazole (yield 73%), with a purity determined by a proton and fluorine RMN higher than 99%.

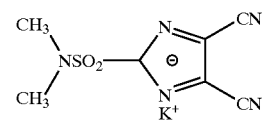

EXAMPLE 15

By operating in a glove box under argon, to 24.15 g (100 mmoles) of di-2-ethylhexylamine in 100 ml of THF at −20°

C., there is added by portions 32 ml is of butyllithium 2 M in cyclohexane (100 mmoles). After one hour, 11.85 g (100 mmoles) of chlorosulfonyl fluoride $FSO_2Cl$ were added. The reaction was continued for 4 hours at −20° C., and during 24 hours at room temperature. The process as in Example 14 was repeated by replacing trifluoromethanesulfonyl chloride with di-2-ethylhexylaminosulfonyl chloride in solution in THF. There is obtained the following compound:

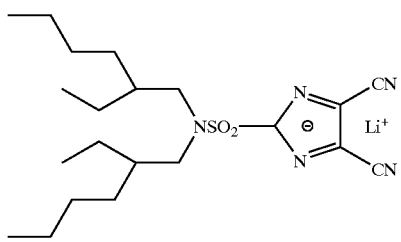

The potassium salt was obtained by treating the lithium salt in a minimum amount of water with potassium fluoride KF. After filtration, evaporation and drying, the potassium salt was recovered in quantitative yield.

These salts are soluble in most of the usual organic solvents (tetrahydrofurane, acetonitrile, dimethylformamide, ethyl acetate, glymes, . . . ) and in aprotic solvating polymers.

EXAMPLE 16

To 13.83 g (100 mmoles) of 1-decyne $C_8H_{17}C{\equiv}CH$ (commercially available from Aldrich) in 100 ml of anhydrous tetrahydrofurane at −20° C., there is added under argon during 30 min, 33.4 ml of a 3 M solution of methylmagnesium chloride (100 mmoles). After 1 hour at −20° C., there is slowly added 30.21 g (100 mmoles) of perfluorobutanesulfonyl fluoride and, after 2 hours at −20° C., there is added by small portions during a period of 1 hour, 6.5 g (100 mmoles) of sodium nitride $NaN_3$. The reaction was continued during 3 hours at −20° C. and during 24 hours at room temperature. The reaction mixture was then stirred during 24 hours with 4.24 g (100 mmoles) of anhydrous lithium chloride LiCl. After centrifugation and filtration of the reaction mixture on a fritted glass of porosity N° 5, there is recovered after drying under vacuum 45.52 g (97% yield) of the lithium salt of 3-decyne-4-trifluoromethanesulfonyl-1,2,3-triazole, with a purity characterized by a proton and fluorine RMN>96%.

Microanalysis has given: H, 3.77 (3,65); Li, 1.46 (1.48); C, 36.45 (35.83); N, 8.85 (8.95); F, 35.99 (36.43); S, 6.75 (6.83).

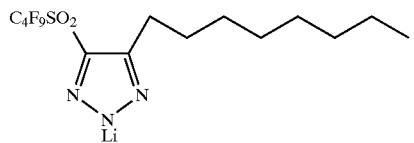

This salt is useful as surfactant. For example, at a concentration as low as 0.1 g/l in water, the surface tension is decreased to a value lower than 25 mN/m.

EXAMPLE 17

In a glove box under argon, to a solution of 1.6 g (20 mmoles) of succinonitrile $NCCH_2CH_2CN$ and 4.52 g (20 mmoles) of 1,1,1,3,5,5,5-heptafluoropentane-2,4-dione $CF_3COCH(F)COCF_3$ in 20 ml of anhydrous THF, there is added by portions 238 mg (30 mmoles) of lithium hydride. After 48 hours, the reaction mixture was filtered, and the solvent was evaporated. The residue was recrystallized in 10 ml of water to which 1.49 g (200 mmoles) of anhydrous potassium chloride has been added. After filtration and drying, 4.38 g (71% yield) of the potassium salt of 1-fluoro-2,5-trifluoromethyl-3,4-dicyano-cyclopentadiene were obtained, with a purity determined by a proton and fluorine RMN higher than 98%.

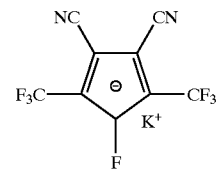

EXAMPLE 18

A solution of 74.08 g (1 mole) of acetylhydrazide $CH_3CONH_2$ and 87.12 g (1 mole) of ethyl acetamidate $CH_3C({=}NH)OC_2H_5$ in 500 ml of ethanol was refluxed during 4 hours. After evaporation of the solvent, the acylamidrazone obtained $CH_3C(=NNHCOCH_3)NH_2$ was melted under vacuum at 110° C. After 24 hours, the product obtained was recrystallized in benzene. After filtration and drying, 59.24 g (61% yield) of 3,5-dimethyl-1H-1,2,4-triazole were recovered, with a purity determined by a proton and carbon RMN higher than 99%.

48.56 g (500 mmoles) of this compound, in solution in 400 ml of carbon tetrachloride $CCl_4$, were then chlorinated, by passing a flow of $Cl_2$ in the solution. After 24 hours, the solvent was evaporated, the product dried, and it was confined in a chemical reactor designed to carry out chemical reactions in anhydrous hydrogen fluoride HF. After flushing the reactor with argon, 500 g of anhydrous hydrogen fluoride (commercially available from Spolchemie, Czech Republic) were introduced. After 72 hours under stirring, hydrogen fluoride was evaporated and the product which was recovered in the reactor was sublimated under vacuum at 40° C. There is then obtained 84 g (82% yield) of 3,5-trifluoromethyl-1H-1,2,4-triazole, with a purity characterized by a proton and fluorine RMN higher than 99%.

The scandium salt was prepared by treating 10 mmoles of this compound, in solution in 10 ml of water, with 1.67 mmoles of scandium acetate. After stirring overnight, water was evaporated and the scandium salt was recovered in quantitative yield after drying.

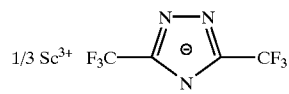

EXAMPLE 19

A solution containing 16.96 (40 mmoles) of lithium 1-(4-styrenesulfonyl)-2,5-trifluoromethyl-3,4-dicyanoimidazole-cyclopentadiene prepared as in Example 8 by replacing stearic acid chloride with 4-styrene-sulfonyl chloride (commercially available from Monomers & Polymers Dajac Laboratories), 3.18 g of acrylonitrile (60 mmoles) and 100 mg of 1,1 '-azobis (cyclohexanecarbonitrile) in 100 ml of anhydrous THF was degassed with a flow of dry argon. The reaction mixture was then heated at 60° C. during 48 hours under argon to copolymerize acrylonitrile with the styrene derivative. After cooling, the solution was concentrated, and the polymer was recovered by reprecipitation in ether. After filtration and drying, the following polymer was obtained:

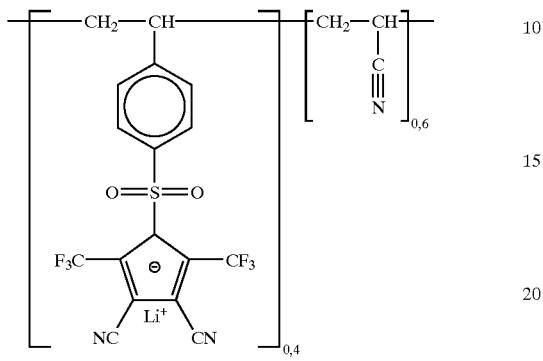

This polymer is useful for gelled polymer electrolytes with fixed anions. It constitutes a matrix in the form of a gel and it behaves as a polyelectrolyte.

An electrochemical generator was mounted by superposing the following layers:

- a current collector of stainless steel with a thickness of 2 mm;
- a composite anode consisting of carbon coke (80% by volume) mixed with said copolymer as binder (20% by volume);
- said gelled copolymer as electrolyte;
- a composite cathode consisting of carbon black (6% by volume), LiCoO$_2$ (75% by volume) and said gelled copolymer (20% by volume);
- an current collector similar to the above mentioned collector.

This generator enabled to carry out 1,000 cycles of charge/discharge between 3 and 4.2 V by keeping a capacity higher than 80% of the capacity during the first cycle, when cycling at 25° C. It has very good performances during calls for power due to the use of fixed anions. Utilization of fixed anions also enable to improve the evolution of the resistance at the interface.

EXAMPLE 20

By a process similar to the one used in Example 19, a copolymer of acrylonitrile (97% molar) and the lithium salt of 1-(4-styrenesulfonyl)-2,5-trifluoromethyl-3,4-dicyanoimidazole-cyclopentadiene (3% molar) was synthesized.

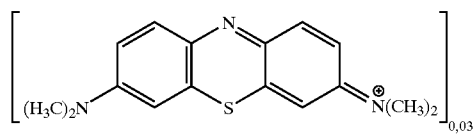

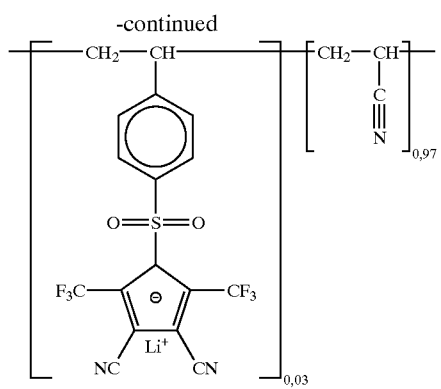

This copolymer in the form of an alkali metal or ammonium salt has antistatic properties and may therefore advantageously replace acrylonitrile copolymers which to this day are widely used in the form of fiber for textiles, but which presents no antistatic properties. Moreover, spinning of this copolymer is easier than that of non-modified PAN.

This copolymer has very good interactions with cationic coloring materials such as methylene blue, which makes it a material of interest for colored textile fibers. The stability of the color is clearly improved as compared to the known copolymer of acrylonitrile and methallylsulfonate.

EXAMPLE 21

To 3.4 g (10 mmoles) of 2-t-butyl-5-heptafluoropropyl-3,4-dicyanocyclopentadiene, obtained in Example 7, and 831 mg (5 mmoles) of 1,1,3,3-tetramethoxypropane in 10 ml of water under stirring, there is added two drops of concentrated sulfuric acid. After 4 hours under stirring, 600 mg of anhydrous lithium carbonate Li$_2$CO$_3$ were added and, after 15 min, there is added 3.22 g (10 mmoles) of tetrabutylammonium bromide (C$_4$H$_9$)4NBr. By extraction with dichloromethane, the following compound was recovered:

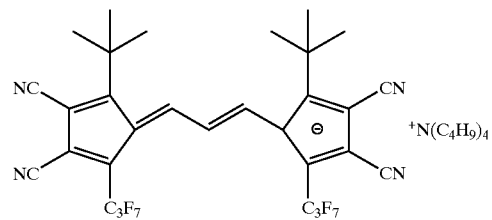

This anionic coloring material of the cyanine family, which is an absorbent in the visible range, is soluble in low polar solvents such as dichloromethane or methylene chloride as well as in low polar polymer matrices such as methyl polymethacrylate. The small level of aggregation of the molecules of this anionic coloring material with one another prevents a phenomenon of widening of the optical absorption bands of this coloring material.

EXAMPLE 22

18.13 g (50 mmoles) of polyoxyethylene-23 lauryl ether (Brij® 30) C$_{12}$H$_{25}$(OCH$_2$CH$_2$)OH and 3.93 g (25 mmoles, commercially available from Aldrich) of 1,2,3-triazole-4,5-dicarboxylic in admixture of 30 ml of THF and 10 ml of pyridine were reacted in the presence of 1.03 g (50 mmoles) of 1,3-dicyclohexylcarbodiimide. After 48 hours, the reaction mixture was filtered to remove the precipitate of dicyclohexylurea, and it was stirred in the presence of 5 g of lithium carbonate Li$_2$CO$_3$. After 48 hours, the reaction mixture was filtered to remove the excess of lithium carbonate and the solvent was evaporated. 20.5 g of the following compound were recovered:

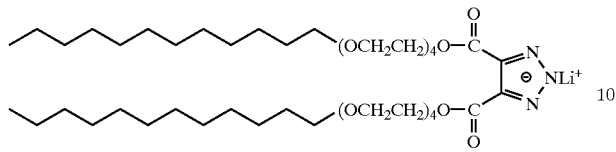

This salt is an excellent surfactant. At a concentration as low as 0.1 g/l in water, the surface tension was decreased to a value lower than 20 mN/m.

EXAMPLE 23

2.54 g of polyaniline chloride (AC&T, St Égrève, France) were suspended in 100 ml of water:

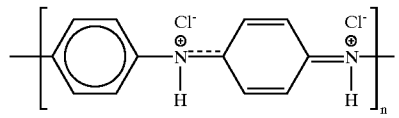

There is then added 9.51 g of potassium trifluoromethanesulfonyl(di-2-ethylhexylaminosulfonyl) imide obtained in Example 15:

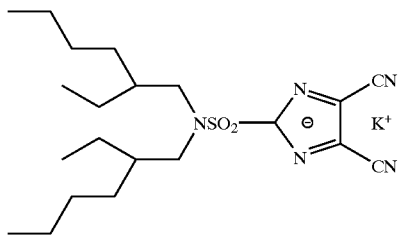

After 48 hours under stirring, a polyaniline doped with di-2-ethylhexylaminosulfonyl-4,5-dicyanoimidazole was recovered. In this form, it is soluble in toluene and it was possible to produce a film from this solution. The thus-doped polyaniline is an electronically conductive polymer which has a conductivity, measured by the method of four points, of 5 S/cm, which is stable in humid medium.

From this solution it was also possible to produce a film on a support of polypropylene (PP) treated by Corona effect. After drying under vacuum at 60° C. during 48 hours, a conductive deposit was obtained which adheres to polyaniline, and has a thickness lower than one micron. This type of treatment on plastic materials is particularly interesting for producing flexible electrical contactors or systems of electromagnetic protections. In addition, this electronically conductive polymer is a good corrosion inhibitor of ferrous metals and aluminum in acid or chloride medium.

EXAMPLE 24

In a three neck flask provided with a cooler, a mechanical stirrer and a neutral gas inlet (Argon), 9.5 g of a copolymer of dimethylsiloxane and (hydrogeno)(methyl)-siloxane (HMS 301 25% SiH, M$_w$ 1900 Gelest Inc., Tullytown, Pa., USA) were suspended in tetrahydrofurane. 7.04 g of lithium 2-(4-ene-1,1-difluorobutyl)-5-cyano-1,3,4-triazole, prepared as in Example 2, and 70 mg of chloroplatinic acid H$_2$PtCl$_6$ were then added. The mixture was heated to reflux during 4 hours. The polymer was then reprecipitated in ethanol.

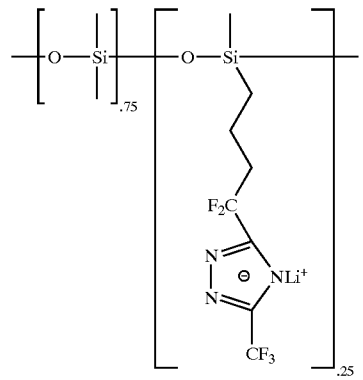

This polymer is soluble in most organic solvents, including in amounts >2% in oils or silicon materials, thus giving them antistatic properties.

EXAMPLE 25

10 mmoles of potassium 2-perfluorobutanesulfonyl-4,5-dicyanoimidazole, obtained in Example 4, and 10 mmoles of di-4,4'-dodecylphenyliodonium (commercially available from General Electric) were stirred together during 24 hours in water. By extraction of the aqueous phase with dichloromethane, the following compound was recovered in quantitative yield after evaporation of dichloromethane and drying:

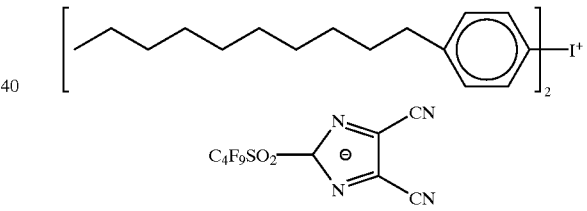

This salt enables to initiate under the effect of actinic radiation (light, γ rays, electron beams) the cationic cross-linking of monomers rich in electrons (vinyl ethers, alkyl vinyl ethers, . . . ). It is soluble in most of the usual organic solvents (tetrahydrofurane, acetonitrile, dimethylformamide, ethyl acetate, glymes, . . . ) and in aprotic solvating polymers such as poly(ethylene oxide). It is also soluble at more that 10% by weight in reactive solvents such as triethyleneglycol divinyl ether.

The photoinitiating properties of this salt were tested by irradiating with U.V. radiation at 254 nm, and a power of 1,900 mW/cm$^2$, a triethyleneglycol divinyl ether solution containing 1% by weight of this salt. After a few seconds under irradiation, the reactive solvent solidified, this reaction being very exothermic.

EXAMPLE 26

4.08 (20 mmoles) of potassium 3,5-bis(trifluoromethyl) pyrazole (commercially available from Aldrich) in 50 ml of anhydrous THF were reacted with 2.17 g (20 mmoles) of 1-chloro-1-ethoxyethane (prepared according to the procedure described by Grummitt & al., *Organic Synthesis*, Wiley, New-York, 1963, Collect. Vol. IV, p 748). After 48 hours under stirring, the reaction mixture was centrifuged to remove the precipitate of potassium chloride KCl. There were then added 8.92 g of perfluoro(4-methyl-3,6-dioxaoct-7-ene)sulfonyl fluoride (commercialized by Apollo Scientific Limited, Stockport, England) and 4.05 g (40 mmoles) of freshly distilled triethylamine. The reaction mixture was then brought to 60° C. during 72 hours and the solvent was evaporated. The residue was recrystallized in 30 ml of water saturated with potassium chloride. After drying, the following compound was recovered:

The corresponding acid was obtained by extracting with ether an aqueous solution of this potassium salt acidified with hydrochloric acid.

A porous GORE-TEX® textile of a thickness of 100 μm, commercially available from Gore, was impregnated with a concentrated dichloromethane solution of said acid containing cyanovaleric acid as polymerization initiator. After evaporation of the solvent, the acid was homopolymerized within the textile matrix by keeping, under argon, the temperature of the mixture at 60° C. during 24 hours. The membrane thus obtained was used as an electrolyte in a test cell of a hydrogen/methanol polymer electrolyte combustible battery. The life of this membrane was longer than 1,000 hours, with a lower permeability to methanol than the one obtained by utilizing a membrane of Nafion® 117 (commercially available from Dupont de Nemours) of the same thickness. Such a membrane may also be used for the Friedel-Crafts heterogeneous catalysis of the acylation reaction of toluene with benzoyl chloride.

EXAMPLE 27

To 10 mmoles of lithium 4-pentafluoro-ethyl-5-cyano-1,2,3-triazole, obtained in Example 12, in solution in 10 ml of water, there is added 12 mmoles of 1-ethyl-3-methyl-1H-imidazolium chloride (commercially available from Aldrich).

There is obtained a liquid phase which is denser than water. This phase was recovered by extraction with dichloromethane. After evaporation of dichloromethane and drying under vacuum at 40° C. of the liquid obtained, the following liquid salt was recovered:

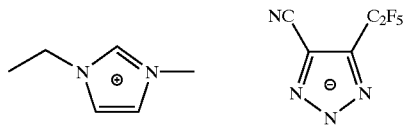

This molten salt has a conductivity of $4.3 \times 10^{-3}$ $S^{-1}.cm^{-1}$ and a freezing point lower than $-10°$ C. Its wide range of redox stability makes it an electrolyte which is particularly interesting for electrochemical generators such as lithium batteries, supercapacitances, systems of modulation of light, photovoltaic cells.

An electrochemical photovoltaic cell similar in principle to the one described in European Patent EP 613466 was prepared. For this purpose, a system made of two electrodes separated by a vacuum space of a thickness of 30 μm was assembled. The first electrode was coated with a nanoparticular layer of titanium dioxide $TiO_2$ 0.25 Jim thick on which cis-dithiocyanato-bis-(2,2'-bipyridyl-4,4'-dicarboxylate ruthenium (II) was adsorbed as sensitizer. The space between the electrodes was filled with an electrolyte made of the molten salt in which 10% by weight of methylhexyl imidazolium iodide and 10 mmoles of iodine were solubilized. With this photovoltaic cell there are obtained interesting performances, and in particular a short-circuit current of 69 $\mu A.cm^{-2}$ and a voltage in open circuit of 512 mV.

This liquid salt may also be used as electrolyte in electrochemical supercapacitances utilizing electrodes of activated carbon or composite electrodes obtained from metallic fibers and carbon fibers treated in reducing atmosphere.

EXAMPLE 28

To 3.2 g (25 mmoles) of 2-(3-thienyl)ethanol in 60 ml of anhydrous dimethylformamide, there is added 7.26 g (25 mmoles) of potassium 1-vinylsulfonyl-2,5-trifluoromethyl-3,4-dicyano-cyclopentadiene, obtained by a process similar to the one described in Example 19, by replacing 4-styrenesulfonyl chloride with ethylenesulfonyl fluoride (commercially available from ACROS), 3.46 g of anhydrous potassium carbonate $K_2CO_3$ (25 mmoles) and 330 mg (1.25 mmoles) of a crown-ether, which is 18-Crown-6 (acting as complexing agent of the potassium cation). The reaction mixture was then stirred under argon at 85° C. After 48 hours, the reaction mixture was filtered on a fritted glass of porosity N° 3, and the solvent was evaporated under reduced pressure. After drying, the compound was recrystallized in 20 ml of water containing 1.86 g (25 mmoles) of anhydrous potassium chloride KCl. After filtration and drying, the following compound was recovered:

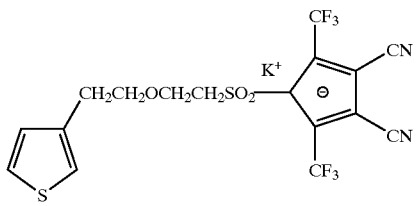

10 ml of a $5 \times 10^{-2}$ M solution of said compound in acetonitrile were prepared and an electropolymerization was carried out in the anode compartment in an electrochemical cell, on the platinum electrode. There is obtained a flexible conductor film of:

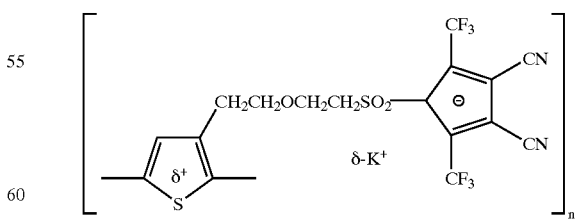

in which doping (oxidation) is ensured by exchange of cations and electrons with the exterior. The conductivity of this material, stable at ambient atmosphere and in humid medium, is of the order of 10 $S.cm^{-1}$. The electropolymerization carried out in the presence of non-substituted pyrrol or a pyrrol having oxyethylene chains in N or 3 position gives copolymers which are equally stable in which the change of color may be used to constitute electrochrome systems.

EXAMPLE 29
Catalysis of an Aldolic Condensation

The catalytic effect of the scandium salt of 3-trifluoromethyl-5-trifluoromethanesulfonyl-1,2,4-triazole, obtained in Example 3, towards an aldolic condensation was evaluated in the following manner: To a solution containing 339 mg (0.4 mmoles) of the scandium salt of 3-trifluoromethyl-5-trifluoromethanesulfonyl-1,2,4-triazole (10% molar) in 15 ml of dichloromethane, there is added a mixture of 1.05 mg (6 mmoles) of 1-ene-2-methyl-1-silylacetal-1-methoxypropene $(CH_3)_2C=C(OSiMe_3)OMe$ and 420 mg (4 mmoles) of benzaldehyde in 10 ml of dichloromethane. After 16 hours under stirring at room temperature, water was added and the product was extracted with dichloromethane. The organic phase was washed with three fractions of 100 ml of water, and dichloromethane was evaporated. The residue was then treated with a tetrahydrofurane/HCl 1 M (20:1) mixture during 0.5 hours at 0C. After diluting with hexane, a saturated solution of sodium bicarbonate was added and the product was extracted with dichloromethane. The organic phase was washed with a saturated solution of sodium chloride, and it was dried with sodium sulfate. After evaporation of the solvents, the raw product was chromatographed on silica gel. Methyl-3-hydroxy-2,2-dimethyl-phenylpropionate was obtained with a yield of 90%.

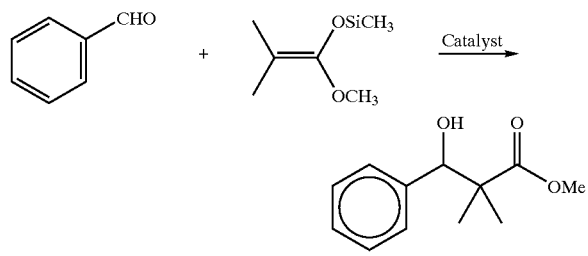

EXAMPLE 30
Catalysis of a Michael Addition

The catalytic effect of the scandium salt of 3-trifluoromethyl-5-trifluoromethanesulfonyl-1,2,4-triazole, obtained in Example 3, with respect to a Michael addition was evaluated in the following manner. To a solution of 339 mg (0.4 mmoles) of scandium 3-trifluoromethyl-5-trifluoromethanesulfonyl-1,2,4-triazole (10% molar) in 15 ml of dichloromethane, there is added a mixture of 1.05 g (6 mmoles) of 1-ene-2-methyl-1-silylacetal-1-methoxypropene $(CH_3)_2C=C(OSiMe3)OMe$ and 840 mg (4 mmoles) of chalcone in 10 ml of dichloromethane. After 12 hours under stirring at room temperature, water is added and the product was extracted with dichloromethane. The organic phase was washed with three fractions of 100 ml of water, and dichloromethane was evaporated. The residue was then treated with a tetrahydrofurane/HCl 1 M (20:1) mixture during 0.5 hours at 0° C. After diluting with hexane, a saturated solution of sodium bicarbonate was added, and the product was extracted with dichloromethane. The organic phase was washed with a saturated solution of sodium chloride, and dried with sodium sulfate. After evaporation of these solvents, the raw product was chromatographed on silica gel. There is obtained a 1,5-dicarbonylated compound with a yield of 89%.

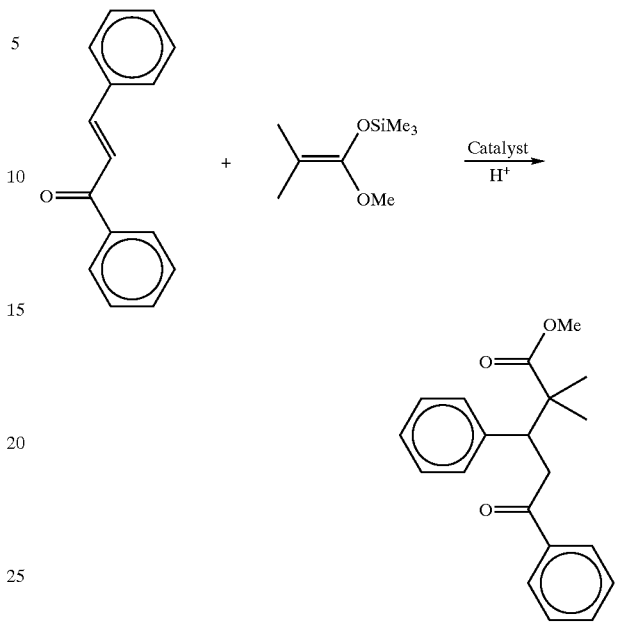

EXAMPLE 31
Catalysis of a Friedel-Crafts Reaction of Acylation

The catalytic effect of the scandium salt of 3-trifluoromethyl-5-trifluoromethanesulfonyl-1,2,4-triazole, obtained in Example 3, relative to a reaction was evaluated in the following manner. In 40 ml of anhydrous nitromethane, there is added 592 mg (700 µmoles) of the scandium salt of 3-trifluoromethyl-5-trifluoromethanesulfonyl-1,2,4-triazole, and 1.08 g (10 mmoles) of anisol and 2.04 g of acetic anhydride. After stirring during 10 min at 21° C., the reaction mixture was diluted with 50 ml of ether and the reaction was inhibited by 100 ml of a saturated solution of sodium bicarbonate $NaHCO_3$. After filtration on Celite, the solution was extracted with three fractions of 50 ml ether, and the collected ether phase was washed with a saturated solution of potassium chloride. After drying the ether phase with magnesium sulfate and evaporation, 1.46 g of p-methoxyacetophenone (97% yield) was collected, with a purity characterized by a proton RMN higher than 99%.

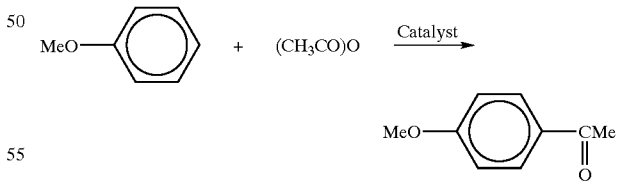

EXAMPLE 32

According to a process similar to the one described in Example 4, the potassium salt of 2-(1R)-(−)-10-camphorsulfonyl-4,5-dicyanoimidazole was obtained by substituting perfluorobutanesulfonyl fluoride with (1R)-(−)-10-camphorsulfonyl (commercially available from Aldrich).

The corresponding lithium salt was obtained by ionic exchange (metathesis) in tetrahydrofurane with lithium chloride.

The scandium salt was obtained by treating the potassium salt with a stoichiometric quantity of scandium tetrafluoroborate $Sc(BF_4)_3$ in acetonitrile. After filtration to remove the precipitate of potassium tetrafluoroborate $KBF_4$ and evaporation of the solvent, the following compound was recovered in quantitative yield;

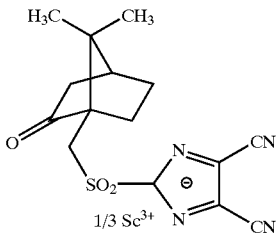

This salt was used as catalyst in a Diels-Alder reaction, namely a reaction of methylvinylketone with cyclopentadiene.

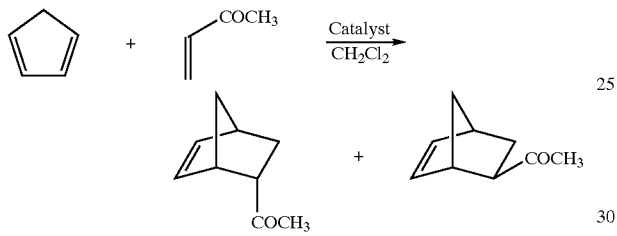

To a solution of 651 mg (10 mmoles) of freshly distilled cyclopentadiene and 701 mg (10 mmoles) of methylvinylketone in 10 ml of dichloromethane there is added 200 μmoles of the chiral scandium salt. After 24 hours at room temperature, the reaction mixture was filtered to remove the catalyst in suspension. The yield of the reaction, determined by chromatography in gaseous phase, is higher than 85%. After separating the various products of the reaction on a chiral column, the enantiomeric excesses were determined by RMN, which has revealed an enantiomeric excess of 73%.

EXAMPLE 33

The lithium salt of 4,5-trifluoromethyl-1,2,3-triazole, obtained in Example 12, was tested in electrochemical generators of lithium-polymer technology.

A battery was produced by superposing the following layers:
 a current collector of stainless steel having a thickness of 2 mm;
 a cathode consisting of a pastil of a film of composite material having a thickness of 72 μm and comprising vanadium dioxide (45% by volume), Shawinigan black (5% by volume) and polyethylene oxide of molecular weight $M_w=3\times10^5$ (50% by volume);
 an electrolyte consisting of a pastil of a poly(ethylene oxide) film of molecular weight $M_w=5\times10^6$ containing said lithium salt at a concentration O/Li=15/1:
 an anode made of a sheet of metallic lithium having a thickness of 50 μm;
 a current collector analogous to the above collector.

The pastils constituting the electrode and electrolyte were cut out in a glove box and piled in the order indicated above. The collectors were then placed on either side of the pile obtained. The assembly was sealed in a housing for a button-shaped battery which simultaneously enables to protect the generator from the atmosphere and to exercise a mechanical stress on the films. The battery was then placed in an enclosure under argon mounted in a drying oven at a temperature of 60° C. It was thereafter cycled between 1.8 and 3.3 V at a rate of charge/discharge of C/10 (nominal capacity charged or discharged in 10 hours). The cycling curve obtained is given in FIG. 1, on which the utilization u, expressed in %, is given in ordinate, and the number of cycles, C, is given in abscissae.

Similar performances were obtained by utilizing:
 the lithium salt of 4-trifluoromethyl-5-cyano-1H-1,2,3-triazole obtained in Example 12;
 the lithium salt of 2-cyano-5-trifluoromethyl-1,3,4-triazole obtained in Example 1;
 the lithium salt of 2-trifluoromethanesulfonyl-5-trifluoromethyl-1,3,4-triazole obtained in Example 3;
 the lithium salt of 2-dimethylaminosulfonyl-4,5-dicyanoimidazole obtained in Example 14;
 the lithium salt of 1-fluoro-2,5-trifluoromethyl-3,4-dicyanocyclopentadiene obtained in Example 17;
 the polysalt of lithium of poly(2-(3,4-epoxy-1,1-difluorobutane)-5-cyano-1,3,4-triazole) obtained in Example 6. In the latter case, the polysalt is introduced at a concentration O/Li=25/1 in the electrolyte and in the cathode. It was possible to note better performances during calls for power due to the fact of the utilization of fixed anions. The utilization of fixed anions also enabled to improve the evolution of the interface resistance.

What is claimed is:

1. An ionically conductive material comprising an ionic compound in a solvent, the said compound comprising at least one anionic part associated to at least one cationic part M in sufficient number to ensure the electronic neutrality of the whole, wherein M is a hydroxonium, a nitrosonium $NO^+$, an ammonium $—NH_4^+$, a metallic cation having a valency m, an organic cation having a valency m, or an organometallic cation having a valency m and in that the anionic part is pentacyclic or derived from tetrazapentalene and corresponds to the following formula:

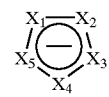

in which the groups $X_1$ is $—N=$, $X_2$ is $—N=$, $X_3$ is $—C(Y_c)—$ with $Y_c$ being $C_nF_{2n+1}$, $X_4$ is $—N—$, and $X_5$ is $—C(Y_c)—$ with $Y_c$ being $SO_2Q—$, and:

Q is a radical selected from:
 alkyl or alkenyl radicals, aryl, arylalkyl, alkylaryl or alkenylaryl radicals, alicyclic or heterocyclic radicals, including polycyclic radicals, said radicals being optionally halogenated or perhalogenated and/or optionally carrying at least one other, thioether, amine, imine, amide, carboxyl, carbonyl, isocyanate, isothiocyanate, hydroxy functional group.

2. A material according to claim 1, characterized in that the organic cation is selected from a group consisting of cations $R_3O^+$, $NR_4^+$, $RC(NHR_2)_2^+$, $C(NHR_2)_3^+$, $C_5R_6N^+$, $C_3R_5N_2^+$, $C_3R_7N_2^+$, $C_2R_4N_3^+$, $SR_3^+$, $PR_4^+$, $IR_2^+$, $(C_6R_5)_3C^+$, the radicals R independently representing an H or a radical selected from the group consisting of:
 alkyl, alkenyl, oxa-alkyl, oxa-alkenyl, aza-alkyl, aza-alkenyl, thiaalkyl, thia-alkenyl, sila-alkyl, sila-alkenyl, aryl, arylalkyl, alkylaryl, alkenylaryl, dialkylamino and dialkylazo radicals;

cyclic or heterocyclic radicals optionally comprising at least one lateral chain comprising heteroatoms such as nitrogen, oxygen, sulfur;

cyclic or heterocyclic radicals optionally comprising heteroatoms in the aromatic nucleus;

groups comprising a plurality of aromatic or heterocyclic nuclei, condensed or non-condensed, optionally containing at least one nitrogen, oxygen, sulfur or phosphorus atom;

with the proviso that a plurality of radicals R may together form aliphatic or aromatic cycles optionally enclosing the center carrying the cationic charge.

3. A material according to claim 2, characterized in that the onium cation is part of the $Y_c$ or the substituent Q.

4. A material according to claim 2, characterized in that the onium cation is part of a recurring unit of a polymer.

5. A material according to claim 2, characterized in that the cation M is a cationic heterocycle with aromatic character, including at least one alkylated nitrogen atom in the cycle.

6. A material according to claim 5, characterized in that the cation is an imidazolium, an imidazolinium, a triazolium, a pyridinium, a 4-dimethylaminopyridinium, said cations optionally carrying a substituent on the carbon atoms of the cycle.

7. A material according to claim 2, characterized in that the cation M is a group having a bond —N=N—, —N=N$^+$, a sulfonium group, an iodonium group, or a substituted or non-substituted arene-ferrocenium cation, optionally incorporated in a polymeric network.

8. A material according to claim 2, characterized in that the cation is a diaryliodonium cation, a dialkylaryliodonium cation, a triarylsulfonium cation, a trialkylaryl sulfonium cation, or a substituted or non-substituted phenacyl-dialkyl sulfonium cation.

9. A material according to claim 8, characterized in that the cation is part of a polymer chain.

10. A material according to claim 2, characterized in that M is an organic cation including a group 2,2'-[azobis(2-2'-imidazolinio-2-yl)propane]$^{2+}$ or 2,2'-azobis(2-amidiniopropane)$^{2+}$.

11. A material according to claim 1 characterized in that the cation M is a metallic cation selected from the group consisting of cations of alkali metals, cations of alkali earth metals, cations of transition metals, cations of trivalent metals, cations of rare earths and organometallic cations.

12. A material according to claim 1, characterized in that the cation is a metallocenium, selected from the group consisting of cations derived from ferrocene, titanocene, zirconocene, indenocenium cations, arene metallocenium cations, cations of transition metals complexed with phosphine ligands optionally having a chirality and organometallic cations having one or more alkyl or aryl groups covalently fixed to an atom or a group of atoms, said cations optionally being part of a polymeric chain.

13. A material according to claim 1, characterized in that the substituent Q is selected from alkyl, alkenyl, oxa-alkyl, oxa-alkenyl, aza-alkyl, aza-alkenyl, thia-alkyl or thia-alkenyl having 1 to 24 carbon atoms, or from aryl, arylalkyl, alkylaryl or alkenylaryl having 5 to 24 carbon atoms, or from alkyl or alkenyl radicals having 1 to 12 carbon atoms and optionally comprising at least one heteroatom O, N or S in the main chain or in a lateral chain, and/or optionally carrying a hydroxy group, a carbonyl group, an amine group, a carboxyl group.

14. Ionically conductive material according to claim 1, characterized in that at least one of the substituents $Y_c$ is a recurring unit of a polymer.

15. Ionically conductive material according to claim 1, characterized in that the solvent is either an aprotic liquid solvent, selected from linear ethers and cyclic ethers, esters, nitriles, nitro derivatives, amides, sulfones, sulfolanes, sulfamides and partially halogenated hydrocarbons, or a polar polymer, or a mixture thereof.

16. Ionically conductive material according to claim 15, characterized in that the solvent is a solvating polymer, cross-linked or non-cross-linked, which may carry grafted ionic groups.

17. Ionically conductive material according to claim 16, characterized in that the solvating polymer is selected from polyethers of linear structure, comb or blocks, which may form a network based on poly(ethylene oxide), copolymers containing the ethylene oxide or propylene oxide or allylglycidylether units, polyphosphazenes, cross-linked networks based on polyethylene glycol cross-linked with isocyanates, networks obtained by polycondensation and carrying groups which enable the incorporation of cross-linkable groups and block copolymers in which certain blocks carry functions with redox properties.

18. Ionically conductive material according to claim 1, characterized in that the solvent essentially consists of an aprotic liquid solvent and a polar polymer solvent comprising units containing at least one heteroatom selected from sulfur, oxygen, nitrogen and fluorine.

19. Ionically conductive material according to claim 18, characterized in that the polar polymer mainly contains units derived from acrylonitrile, vinylidene fluoride, N-vinylpyrrolidone or methyl methacrylate.

20. Ionically conductive material according to claim 1, characterized in that it additionally contains at least one second salt.

21. Ionically conductive material according to claim 1, characterized in that it additionally contains a mineral or organic filler in the form of powder or fibers.

22. Electrochemical generator comprising a negative electrode and a positive electrode both separated by an electrolyte, characterized in that the electrolyte is a material according to claim 1.

23. Generator according to claim 22, characterized in that the negative electrode consists of metallic lithium, or an alloy thereof, optionally in the form of nanometric dispersion in lithium oxide, or a double nitride of lithium and a transition metal, or an oxide with low potential having the general formula $Li_{1+y+x/3}Ti_{2-x/3}O_4$ ($0 \leq x \leq 1$, $0 \leq y \leq 1$), or carbon and carbonated products produced by pyrolysis of organic material.

24. Generator according to claim 22, characterized in that the positive electrode is selected from vanadium oxides $VO_x$ ($2 \leq x \leq 2.5$), $LiV_3O_8$, $Li_yNi_{1-x}Co_xO_2$, ($0 \leq x \leq 1$; $0 \leq y \leq 1$), spinels of manganese $Li_yMn_{1-x}M_xO_2$ (M=Cr, Al, V, Ni, $0 \leq x \leq 0.5$; $0 \leq y \leq 2$), organic polydisulfides, FeS, $FeS_2$, iron sulfate $Fe_2(SO_4)_3$, phosphates and phosphosilicates of iron and lithium of olivine structure, or substituted products wherein iron is replaced by manganese, used alone or in mixtures.

25. Generator according to claim 22, characterized in that the cathode collector is made of aluminum.

26. Supercapacitor utilizing at least one carbon electrode with high specific surface, or an electrode containing a redox polymer, in which the electrolyte is a material according to claim 1.

27. A process for doping, p or n, a polymer with electronic conduction, said process comprising utilizing a material according to claim 1.

28. Electronically conductive material characterized in that it comprises a material according to claim 1.

29. Process of polymerization or cross-linking of monomers or prepolymers capable of cationic reaction, characterized in that there is used a material according to claim 1 as photoinitiator constituting a source of acid catalyzing the reaction.

30. Process according to claim 29, characterized in that the monomers are selected from the group consisting of compounds which include a cyclic ether function, a cyclic thioether function or a cyclic amino function, vinyl compounds, vinyl ethers, oxazolines, lactones and lactames.

31. Process according to claim 29, characterized in that the prepolymer is selected from the group consisting of compounds in which epoxy groups are carried by an aliphatic chain, an aromatic chain, or a heterocyclic chain.

32. Process according to claim 29, characterized in that it consists in mixing the photoinitiator with at least one monomer or prepolymer capable of cationic polymerization and subjecting the mixture obtained to actinic radiation.

33. Process according to claim 32, characterized in that the reaction mixture is subject to radiation after having been formed into a thin layer.

34. Process according to claim 29, characterized in that the photoinitiator is used in the form of a solution in a solvent which is inert towards the polymerization reaction.

35. Process according to claim 34, characterized in that the inert solvent is selected from the group consisting of acetone, methylethyl ketone, acetonitrile, propylene carbonate, γ-butyrolactone, ether-esters of mono-, di-, tri-ethylene or propylene glycols, ether-alcohols of mono-, di-, tri-ethylene or propylene glycols, esters of phthalic acid or of citric acid.

36. Process according to claim 29, characterized in that the reaction is carried out in the presence of a solvent or a diluent consisting of a compound which is reactive towards polymerization.

37. Process according to claim 36, characterized in that the reactive compound is selected from the group consisting of vinyl mono- and di- ethers of mono-, di-, tri-, tetra-ethylene or propylene glycols, trivinyl ether trimethylolpropane and divinyl ether of dimethanolcyclohexane, N-vinylpyrolidone, 2-propenylether of propylene carbonate.

38. Process according to claim 29, characterized in that a photosensitizer is added to the reaction mixture.

39. Process according to claim 38, characterized in that the photosensitizer is selected from the group consisting of anthracene, diphenyl-9,10-anthracene, perylene, phenothiazine, tetracene, xanthone, thioxanthone, isopropylthioxanthone, acetophenone, benzophenone, 1,3,5-triaryl-2-pyrazolines and derivatives thereof.

40. Process according to claim 29, characterized in that the reaction mixture additionally contains at least one monomer or prepolymer capable of free radical polymerization and a compound capable of releasing a free radical polymerization initiator under the effect of actinic radiation or β radiation or under the action of heat.

41. Process of modifying properties of solubility of a polymer having groups sensitive towards acids, characterized in that it consists in subjecting said polymer to actinic radiation or β radiation, in the presence of an ionically conductive material comprising an ionic compound in a solvent, the said compound comprising at least one anionic part associated to at least one cationic part M in sufficient number to ensure the electronic neutrality of the whole, wherein M is a hydroxonium, a nitosonium $NO^+$, an ammonium $—NH_4^+$, a metallic cation having a valency m, an organic cation having a valency m, or an organometallic cation having a valency m and in that the anionic part is pentacyclic or derived from tetrazapentalene and corresponds to one of the following formulae:

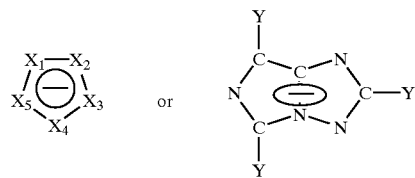

in which the groups $—X_i—$ represent independently from one another a group selected from $—N=$, $—N—$, $—C(Y_c)=$, $—C(Y_c)—$, $—S(=O)(Qs)=$, $—S(Qs)=$ or $—P(Q')(Q'')=$, wherein among the five groups $—X_i—$ forming the ring, no $—X_i—$ represents $—N=$ or $—N^-$, or at least two $—X_i—$ represent independently $—N=$ or $—N^+—$, at most four groups $—X_i—$ comprise an hydrogen atom, at most two groups $—X_i—$ comprise a sulfur atom provided they are not adjacent on the ring, at most one group $—X_i—$ comprise a phosphorus atom, and:

Q' and Q'' represent independently from one another a $C_1$–$C_8$ perhaloalkyl or perhaloalkenyl radical a $C_6$–$C_{12}$ aryl or alkylaryl radical, optionally halogenated, each may contain oxa, thia, aza substituents;

Qs is a radical selected from:
a) alkyl or alkenyl radicals, aryl, arylalkyl, alkylaryl or alkenylaryl radicals, alicyclic or heterocyclic radicals, including polycyclic radicals, said radicals being optionally halogenated or perhalogenated and/or optionally carrying at least one ether, thioether, amine, imine, amide, carboxyl, carbonyl, isocyanate, isothiocyanate, hydroxy functional group;
b) monocyclic, polycyclic or condensed aromatic radicals in which the aromatic nuclei and/or at least one substituent of a nucleus comprise heteroatoms;
c) polymer radicals;
d) radicals having one or more cationic ionophoric groups and/or one or more anionic ionophoric groups;

$Y_c$ or Y represent H, or a group attracting electrons selected from the group consisting of:
F, Cl, Br, $—C\equiv N$, $—S—C\equiv N$, $—N=C=S$, $—N=C=O$, $—NO_2$, $C_nF_{2n+1}—C_nF_{2n+1}—O—$, $C_nF_{2n+1}—CH_2—$, $—OC_2F_4H$, $—SCF_3$, $—SC_nF_{2n+1}$, $—SC_2F_4H$, $—O—CF=CF_2$, $—SCF=CF_2$, $FSO_2$;
radicals $QSO_2—$, $—CO_2Q$, $Q—N—SO_2—$, $QCO—$, in which Q is selected from the substituents defined above for $Q_s$;
radicals comprising one or more aromatic nuclei optionally containing at least one nitrogen, oxygen, sulfur or phosphorus atoms, said nuclei may optionally be condensed nuclei and/or the nuclei may optionally carry at least one substituent selected from halogens, $—CN$, $—NO_2$, $—SCN$, $—N_3$, $CF_2=CF—O—$, radicals $R_F—$ and $R_FCH_2—$ in which $R_F$ is a perfluoroalkyl radical having 1 to 12 carbon atoms, fluoroalkyloxy groups, fluoroalkylthioxy groups, alkyl, alkenyl, oxa-alkyl, oxaalkenyl, aza-alkyl, aza-alkenyl, thia-alkyl, thia-alkenyl radicals, polymer radicals, radicals having at least one cationic ionophoric group and/or at least one anionic ionophoric group;

or two substituents selected from $Y_c$, $Q_s$, Q' and Q'' of a pentacyclic anionic group on the one hand, or two substituents Y of an anionic group derived from tetrazapentalene on the other hand, together form a ring having 4 to 8 chains, said ring optionally being of aromatic conjugated nature;

or one of the substituents Y, $Y_c$ or $Q_s$ is a multivalent radical (including a dendrimer) connected to at least another pentacyclic anionic group or to at least another anionic group derived from tetrazapentalene;

or one of the substituents Y, $Y_c$ or $Q_s$ represent a recurring unit of a polymer.

42. Process according to claim 41, characterized in that the polymer contains ester units or arylether units derived from a tertiary alcohol.

43. Process according to claim 42, characterized in that the polymer is selected from the group consisting of homopolymers and copolymers of tert-butyl or tert-amyl, (tert-butoxycarbonyloxystyrene) or (tert-amyloxystyrene) itaconate.

44. Process according to claim 41, characterized in that it is used for the chemical amplification of photoresists.

45. A laser or optical disk containing a composition or photographic film having a sensitizer containing a composition in which the composition contains cationic coloring material, characterized in that it contains an ionically conductive material comprising an ionic compound, the said compound comprising at least one anionic part associated to at least one cationic part M in sufficient number to ensure the electronic neutrality of the whole, wherein M is a hydroxonium, a nitrosonium $NO^+$, an ammonium $—NH_4^+$, a metallic cation having a valency m, an organic cation having a valency m, or an organometallic cation having a valency m and in that the anionic part is pentacyclic or derived from tetrazapentalene and corresponds to one of the following formulae:

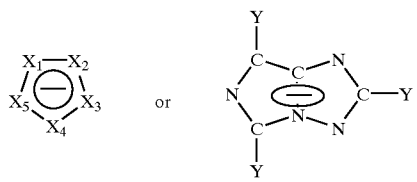

in which the groups $—X_i—$ represent independently from one another a group selected from $—N=$, $—N—$, $—C(Y_c)=$, $—C(Y_c)—$, $—S(=O)(Qs)=$, $—S(Qs)=$ or $—P(Q')(Q'')=$, wherein among the five groups $—X_i—$ forming the no $—X_i—$ represents $—N=$ or $—N^-$, or at least two $—X_i—$ represent independently $—N=$ or $—N^+—$, ring at most four groups $—X_i—$ comprise an hydrogen atom, at most two groups $—X_i—$ comprise a sulfur atom provided they are not adjacent on the ring, at most one group $—X_i—$ comprise a phosphorus atom, and:

Q' and Q'' represent independently from one another a $C_1$–$C_8$ perhaloalkyl or perhaloalkenyl radical, a $C_6$–$C_{12}$ aryl or alkylaryl radical, optionally halogenated, each may contain oxa, thia, aza substituents;

Qs is a radical selected from:
a) alkyl or alkenyl radicals, aryl, arylalkyl, alkylaryl or alkenylaryl radicals, alicyclic or heterocyclic radicals, including polycyclic radicals, said radicals being optionally halogenated or perhalogenated and/or optionally carrying at least one ether, thioether, amine, imine, amide, carboxyl, carbonyl, isocyanate, isothiocyanate, hydroxy functional group;
b) monocyclic, polycyclic or condensed aromatic radicals in which the aromatic nuclei and/or at least one substituent of a nucleus comprise heteroatoms;
c) polymer radicals;
d) radicals having one or more cationic ionophoric groups and/or one or more anionic ionophoric groups;

$Y_c$ or Y represent H, or a group attracting electrons selected from the group consisting of:
F, Cl, Br, $—C\equiv N$, $—S—C\equiv N$, $—N=C=S$, $—N=C=O$, $—NO_2$, $C_nF_{2n+1}$—$C_nF_{2n+1}$—O—, $C_nF_{2n+1}$—$CH_2$—, $—OC_2F_4H$, $—SCF_3$, $—SC_nF_{2n+1}$, $—SC_2F_4H$, $—O—CF=CF_2$, $—SCF=CF_2$, $FSO_2$;

radicals $QSO_2$—, $—CO_2Q$, Q—N—$SO_2$—, QCO—, in which Q is selected from the substituents defined above for $Q_s$;

radicals comprising one or more aromatic nuclei optionally containing at least one nitrogen, oxygen, sulfur or phosphorus atoms, said nuclei may optionally be condensed nuclei and/or the nuclei may optionally carry at least one substituent selected from halogens, —CN, $—NO_2$, —SCN, $—N_3$, $CF_2=CF$—O—, radicals $R_F$— and $R_FCH_2$— in which $R_F$ is a perfluoroalkyl radical having 1 to 12 carbon atoms, fluoroalkyloxy groups, fluoroalkylthioxy groups, alkyl, alkenyl, oxa-alkyl, oxaalkenyl, aza-alkyl, aza-alkenyl, thia-alkyl, thia-alkenyl radicals, polymer radicals, radicals having at least one cationic ionophoric group and/or at least one anionic ionophoric group;

or two substituents selected from $Y_c$, $Q_s$, Q' and Q'' of a pentacyclic anionic group on the one hand, or two substituents Y of an anionic group derived from tetrazapentalene on the other hand, together form a ring having 4 to 8 chains, said ring optionally being of aromatic conjugated nature;

or one of the substituents Y, $Y_c$ or $Q_s$ is a multivalent radical (including a dendrimer) connected to at least another pentacyclic anionic group or to at least another anionic group derived from tetrazapentalene;

or one of the substituents Y, $Y_c$ or $Q_s$ represent a recurring unit of a polymer.

46. A laser or optical disk or photographic film of cationic coloring material according to claim 45, characterized in that the negative charge(s) of the pentacyclic anionic group or derived from tetrazapentalene are either fixed to the molecule of coloring material, or they constitute the counter-ion of positive charge of the coloring material.

47. A process of using an ionic compound in a catalytic reaction, said reaction selected from the group consisting of Friedel-Craft reactions, reactions of Diels and Alder, Michael additions, reactions of allylation, reactions of pinacolic coupling, reactions of glycosilation, reactions of openings of cycles of oxetanes, reactions of aldolization, reactions of metathesis of alkenes, Ziegler-Natta polymerizations, ring opening metathesis polymerizations and metathesis polymerizations of acyclic dienes, said process comprising adding a material of claim 1 to a reaction mixture.

48. A process according to claim 47, characterized in that the compound in the material is a compound according to claim 1 in which the cation is selected from lithium, magnesium, copper, zinc, tin, trivalent metals, including rare earths, platinoids, and organometallic cations.

49. Electrochrome device in which the electrolyte is an ionically conductive material comprising an ionic compound in a solvent, the said compound comprising at least one anionic part associated to at least one cationic part M in sufficient number to ensure the electronic neutrality of the whole, wherein M is a hydroxonium, a nitrosonium $NO^+$, an ammonium —NH$_4^+$, a metallic cation having a valency m, an organic cation having a valency m, or an organometallic cation having a valency m and in that the anionic part is pentacyclic or derived from tetrazapentalene and corresponds to one of the following formulae:

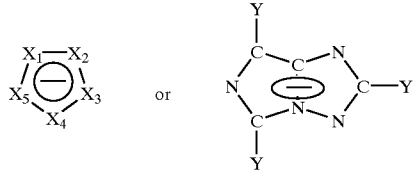

in which the groups —X$_i$— represent independently from one another a group selected from —N=, —N—, C(Y$_c$)=, —C(Y$_c$)—, —S(=O)(Qs)=, —S(Qs)= or —P(Q')(Q")=, wherein among the five groups —X$_i$— forming the ring, no —X$_i$— represents —N= or —N$^-$, or at least two —X$_i$— represent independently —N= or —N$^+$, at most four groups —X$_i$— comprise an hydrogen atom, at most two groups —X$_i$— comprise a sulfur atom provided they are not adjacent on the ring, at most one group —X$_i$— comprise a phosphorus atom, and:

Q' and Q" represent independently from one another a C$_1$–C$_8$ perhaloalkyl or perhaloalkenyl radical, a C$_6$–C$_{12}$ aryl or alkylaryl radical, optionally halogenated, each may contain oxa, thia, aza substituents;

Qs is a radical selected from:
a) alkyl or alkenyl radicals, aryl, arylalkyl, alkylaryl or alkenylaryl radicals, alicyclic or heterocyclic radicals, including polycyclic radicals, said radicals being optionally halogenated or perhalogenated and/or optionally carrying at least one ether, thioether, amine, imine, amide, carboxyl, carbonyl, isocyanate, isothiocyanate, hydroxy functional group;
b) monocyclic, polycyclic or condensed aromatic radicals in which the aromatic nuclei and/or at least one substituent of a nucleus comprise heteroatoms;
c) polymer radicals;
d) radicals having one or more cationic ionophoric groups and/or one or more anionic ionophoric groups:

Y$_c$ or Y represent H, or a group attracting electrons selected from the group consisting of:
F, Cl, Br, —C≡N, —S—C≡N, —N=C=S, —N=C=O, —NO$_2$, C$_n$F$_{2n+1}$—C$_n$F$_{2n+1}$—O—, C$_n$F$_{2n+1}$—CH$_2$—, —OC$_2$F$_4$H, —SCF$_3$, —SC$_n$F$_{2n+1}$, —SC$_2$F$_4$H, —O—CF=CF$_2$, —SCF=CF$_2$, FSO$_2$;
radicals QSO$_2$—, —CO$_2$Q, Q—N—SO$_2$—, QCO—, in which Q is selected from the substituents defined above for Q$_s$;

radicals comprising one or more aromatic nuclei optionally containing at least one nitrogen, oxygen, sulfur or phosphorus atoms, said nuclei may optionally be condensed nuclei and/or the nuclei may optionally carry at least one substituent selected from halogens, —CN, —NO$_2$, —SCN, —N$_3$, CF$_2$=CF—O—, radicals R$_F$— and R$_F$ CH$_2$— in which R$_F$ is a perfluoroalkyl radical having 1 to 12 carbon atoms, fluoroalkyloxy groups, fluoroalkylthioxy groups, alkyl, alkenyl, oxa-alkyl, oxaalkenyl, aza-alkyl, aza-alkenyl thia-alkyl, thia-alkenyl radicals, polymer radicals, radicals having at least one cationic ionophoric group and/or at least one anionic ionophoric group;

or two substituents selected from Y$_c$ Q$_s$, Q' and Q" of a pentacyclic anionic group on the one hand, or two substituents Y of an anionic group derived from tetrazapentalene on the other hand, together form a ring having 4 to 8 chains, said ring optionally being of aromatic conjugated nature;

or one of the substituents Y, Y$_c$ or Q$_s$ is a multivalent radical (including a dendrimer) connected to at least another pentacyclic anionic group or to at least another anionic group derived from tetrazapentalene;

or one of the substituents Y, Y$_c$ or Q$_s$ represent a recurring unit of a polymer.

* * * * *

UNITED STATES PATENT AND TRADEMARK OFFICE
CERTIFICATE OF CORRECTION

PATENT NO.   : 6,395,367 B1                                                    Page 1 of 1
DATED        : May 28, 2002
INVENTOR(S)  : Michot et al.

It is certified that error appears in the above-identified patent and that said Letters Patent is hereby corrected as shown below:

Column 36,
Line 57, the term "other" should read -- ether --.

Column 40,
Line 43, "II," should read -- H, --.

Signed and Sealed this

Third Day of December, 2002

JAMES E. ROGAN
*Director of the United States Patent and Trademark Office*